US008084230B2

(12) United States Patent
Moore et al.

(10) Patent No.: US 8,084,230 B2
(45) Date of Patent: Dec. 27, 2011

(54) TRIMERIZING POLYPEPTIDES

(75) Inventors: Margaret Dow Moore, Seattle, WA (US); Brian A. Fox, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 171 days.

(21) Appl. No.: 12/686,896

(22) Filed: Jan. 13, 2010

(65) Prior Publication Data

US 2010/0297701 A1 Nov. 25, 2010

Related U.S. Application Data

(62) Division of application No. 11/530,672, filed on Sep. 11, 2006, now Pat. No. 7,655,439.

(60) Provisional application No. 60/715,883, filed on Sep. 9, 2005.

(51) Int. Cl.
*C12P 21/06* (2006.01)

(52) U.S. Cl. .................................................... 435/69.1

(58) Field of Classification Search .................. 435/69.1
See application file for complete search history.

(56) References Cited

U.S. PATENT DOCUMENTS

| | | | |
|---|---|---|---|
| 6,190,886 | B1 | 2/2001 | Hoppe et al. |
| 6,911,205 | B2 | 6/2005 | Sodroski et al. |

FOREIGN PATENT DOCUMENTS

| | | |
|---|---|---|
| WO | 2004/033486 | 4/2004 |

OTHER PUBLICATIONS

Amdt et al., "Comparison of In Vivo Selection and Rational Design of Heterodimeric Coiled Coils," *Structure*, vol. 10, pp. 1235-1248, Sep. 2002.

Benit et al., "Identification, Phylogeny, and Evolution of Retroviral Elements Based on Their Envelope Genes," *Journal of Virology*, vol. 75, No. 12, pp. 11709-11719, Dec. 2001.

Bullough et al., "Structure of influenza haemagglutinin at the pH of membrane fusion," *Nature*, vol. 371, pp. 37-43, Sep. 1, 1994.

Cheynet et al., "Synthesis, Assembly, and Processing of the Env ERVWE1/Syncytin Human Endogenous Retroviral Envelope," *Journal of Virology*, pp. 5585-5593, May 2005.

Fass et al., "Retrovirus envelope domain at 1.7 A resolution," *Nature Structural Biology*, vol. 3, No. 5, pp. 465-469, May 5, 1996.

Fass and Kim, "Dissection of a retrovirus envelope protein reveals structural similarity to influenze hemagglutinin," *Current Biology*, vol. 5, No. 12, pp. 1377-1383, 1995.

Harbury et al., "High-Resolution Protein Design with Backbone Freedom," *Science*, vol. 282, pp. 1462-1467, Nov. 20, 1998.

McGrew et al., "Expression of Trimeric CD40 ligand in *Pichia pastorisis*: use of a rapid method to detect high-level expressing transformants," *Gene: An International Journal on Genes and Genomes*, vol. 187, No. 2, pp. 193-200, Mar. 18, 1997.

Muller et al., "Protein Fusions to Coiled-Coil Domains," *Methods in Enzymology*, vol. 328, pp. 261-283, 2000.

Ogihara et al., "The crystal structure of the designed trimeric coiled coil coil-$V_aL_d$: Implications for engineering crystals and supramolecular assemblies," *Protein Science*, vol. 6, pp. 80-88, 1997.

Thomas et al., "A trimeric alpha-helical, coiled coil peptide: association stoichiometry and interaction strength by analytical ultracentrifugation," *Eur Biophys J.*, vol. 25, pp. 405-410-, 1997.

Wagschal et al., "De Novo Design of a Model Peptide Sequence to Examine the Effects of Single amino Acid Substitutions in the Hydrophobic Core on both Stability and Oligomerization State of Coiled-coils," *J. Mol. Biol.*, vol. 285, pp. 785-803, 1999.

Chambers et al., "Heptad Repeat Sequences are Located Adjacent to Hydrophobic Regions in Several Types of Virus Fusion Glycoproteins," *Journal of General Virology, Society for General Microbiology*, vol. 71, No. Part 12, pp. 3075-3080, Dec. 1990.

Delwart et al., "Retroviral Envelope Glycoproteins Contain a Leucine Zipper-Like Repeat," *Aids Research and Human Retroviruses*, vol. 6, No. 6, pp. 703-706, Jun. 1990.

*Primary Examiner* — Maryam Monshipouri
(74) *Attorney, Agent, or Firm* — Michelle L. Lewis

(57) ABSTRACT

The present invention relates to a method of preparing a trimeric protein comprising culturing a host cell transformed or transfected with an expression vector encoding a fusion protein comprising a ZymoZipper (ZZ) domain and a heterologous protein. In one embodiment, the heterologous protein is a membrane protein, the portion of the heterologous protein that included in the fusion protein is the extracellular domain of that protein, and the resulting fusion protein is soluble. In another embodiment of the present invention, the ZZ domain is derived from the transmembrane (TM) subunit of a virus envelope protein or another heptad repeat containing gene of a virus genome. The method can be used to produced homo- and hetero-trimeric proteins. The present invention also encompasses DNA molecules, expression vectors, and host cells used in the present method and fusion proteins produced by the present method.

12 Claims, 5 Drawing Sheets

TRIMERIZING POLYPEPTIDES

This application is a divisional of U.S. patent application Ser. No. 11/530,672, filed Sep. 11, 2006, now U.S. Pat. No. 7,655,439, which claims the benefit of U.S. Provisional Application Ser. No. 60/715,883, filed Sep. 9, 2005, which are herein incorporated by reference in their entirety.

BACKGROUND OF THE INVENTION

The present invention relates to polypeptides able to form multimers, particularly trimers, and the manufacture and use of such polypeptides.

A. Coiled-Coils

A basic component of the quaternary structure of the present multimerizing polypeptides is the coiled-coil (reviewed in Müller et al., (2000) Meth. Enzymol. 328: 261-283). Coiled-coils are protein domains that take the shape of gently twisted, ropelike bundles. The bundles contain two to five a helices in parallel or antiparallel orientation. The essential feature of coiled-coil sequences is a seven-residue, or heptad, repeat $(abcdefg)_n$ with the first (a) and fourth (d) positions commonly occupied by hydrophobic amino acids. The remaining amino acids of the coiled-coil structure are generally polar, where proline is usually excluded due to its disruptive effect on helical architecture.

This characteristic heptad repeat (also known as a 3,4 hydrophobic repeat) is what forms the structure of the coiled-coil domain, with each residue sweeping about 100°. This results in the seven residues of the heptad repeat falling short of two full turns by 20°. The lag forms a gentle, left-handed hydrophobic stripe of residues running down an a helix and the coiled-coil forms when these hydrophobic stripes associate. Deviations from the regular 3,4 spacing of nonpolar residues changes the angle of the hydrophobic stripe with respect to the helix axis, altering the crossing angle of the helices and destabilizing the quaternary structure. An example of a common means of diagramming coiled-coil heptad repeats is illustrated in FIG. 1.

Parallel dimers and trimers are the most common observed coiled-coil structures. The features that distinguish dimers from trimers from higher order oligomerization formations are relatively well understood. The core residues of the heptad repeat (residues a and d) largely determine the oligomerization state, while residues on the edge of the helix (e and g) play secondary roles. Trimers are the default organization for a random distribution of core residues as other oligomerization states cannot tolerate β-branched amino acids (Ile, Val, and Thr) in the d position for dimers or the a position for tetramers. In contrast, trimers generally permit the presence of β-branched and other hydrophobic amino acids in the core positions.

Coiled-coil fusions have been used to achieve diverse experimental goals. One common use is the replacement of natural oligomerization domains with a heterologous sequence to alter oligomerization state, stability, and/or avidity. Low affinity monomers that do not naturally associate can be oligomerized in order to bind effectly to other multimeric targets. Additionally, the oligmerization domain fusion can be used to mimic the activated state of the native protein that is difficult to achieve with recombinant protein production (see, e.g., Pullen et al. (1999) Biochem. 94:6032). This approach has been particularly effective when producing only specific domains, such as the extracellular (cytoplasmic) or intracellular portion of a protein of interest. Commonly, coiled-coils are genetically fused to the protein of interested via a flexible linker that will provide access for the fusion to a large three-dimensional space. Direct fusions are used for experimental goals that require more rigid molecules, such as those used for crystallization.

A number of model coiled-coil systems have been developed based on the structural information of large structural proteins, such as myosin and tropomyosin (TM43, Lau et al. J Biol Chem; 259: 13253-13261), a group of proteins known as collectins (Hoppe et al. (1994) Protein Sci; 3:1143-1158), or of the dimerization region of DNA regulatory proteins, such as the yeast transcriptional activator protein GCN4-p1 (Landschulz et al. (1988) Science; 240:1759-1764). This last structure is often referred to as a "leucine zipper" or LZ. Derivative model systems from the TM43 have been made, specifically where one leucine per heptad has been switched to phenylalanine. This structure is known as a "phenylalanine zipper" or FZ (Thomas et al. Prog Colloid Polymer Sci; 99: 24-30). A third type of well-known derivative of the LZ is the isoleucine zipper (IZ) (Harbury et al. (1994) Nature 371:80-83).

An important constraint of model coiled-coils is the ability to be produced in the expression host. The lack of disulfide bonds in coiled-coil structures aids their production in heterologous expression systems. However, de novo designed sequences tend to be sensitive to proteolysis. Even if effectively expressed, the relative lack of effectiveness as compared to natural sequences reflects the gaps in the current knowledge about all variables involved in protein interaction (Arndt et al. (2002) Structure 10: 1235-1248). Additionally, the use of model sequences is problematic when the goal of the fusion protein produced is a biologically functional protein.

B. Viral Heptad Repeats

Many viruses produce a fusogenic form of viral envelope glycoproteins. Among the viral genuses or families that exhibit this type of fusion proteins are Orthomyxovirus (for example, Influenza virus), Filovirus (Ebola virus), Betaretrovirus (Mason Pfizer Monkey Virus (MPMV)), Gammaretrovirus (Friend Murine Leukemia Virus (FRMLV); Moloney Murine Leukemia Virus (MoMLV)), Deltraretrovirus (Human T-cell Leukemia Virus type 1 (HTLV-1)) and Lentivirus (Human Immunodeficiency Virus type 1 (HIV-1) and Simian Immunodeficiency Virus (SIV)) (reviewed in Cheynet et al. (2005) J Virol; 79; 5585-5593). In these viruses, the transmembrane subunit is produced as a fusion protein, encoded by the env gene. This gene product is cleaved into two proteins, the surface protein which is involved in receptor recognition, and the transmembrane subunit, which anchors the whole env complex to the membrane and is involved in virus entry through membrane fusion. These proteins are characterized by the presence of heptad repeats within the TM region which form strong interactions between oligomers of the protein via the formation of a coiled-coil structure with three subunits (Li et al. (1996) J Virol; 70: 1266-1270; Tucker et al. (1991) Virol; 185:710-720).

Crystal structures of several TM proteins have been determined: MoMLV (Fass et al. (1996) Nat Struc Biol; 3:465-469); HIV-1 (Chan et al. (1997) Cell; 89: 263-273); HTLV-1 (Kobe et al. (1999) PNAS; 93:4319-4324). Similar structures were also found in influenza virus (Wilson et al. (1981) Nature; 289: 366-373) and Ebola virus (Malashkevich et al. (1999) PNAS; 96:2662-2667) and this structure has been hypothesized to reflect a common mechanism for the fusion process and viral entry (Chambers et al. J Gen Virol; 71: 3075-3080). Other viruses that include heptad repeats within their genome are Cornaviruses (Severe Acute Respiratory Syndrome-associated cornavirus (SARS-CoV)) (Bosch et al. J Virol 77: 8801-8811); Herpesvirus (herpes virus simplex 1

(HSV-1) (Gianni et al. (2005) J Virol 79:7042-7049) and Human Cytomegalovirus (CMV)) (Lopper et al. J Virol (2004) 78: 8333-8341); and Paramyoxvirus (measles virus) (Buckland et al. (1992) J Gen Virol 73:1703-1707).

Sequence homology in the TM region has also allowed for the identification of endogenous retroviruses in sequence databases. These searches have been performed and have successfully identified endogenous retroviruses in many organism genomes, including human, rat, and mouse. One well known example of a family of human endogenous retroviruses (HERVs) is HERV-W. One locus of this family, ERVWE1 has been shown to encode a full length env open reading frame and produces a protein also known as syncytin (Cheynet et al. (2005) J Virol; 79:5585-5593). Like the viral protein, this protein is produced and cleaved into two separate subunits, a gp50 surface subunit and a gp24 transmembrane subunit. The gp24 subunit includes heptad repeats and the subunits are found associated as homotrimers. Interestingly, this protein is naturally produced in the placenta and may be involved in cell-cell interactions such as the fusion of the placenta to the uterine wall.

There remains a need in the art to adapt natural trimerization sequences for use in the production of biologically active, recombinant fusion proteins. Accordingly, the present application describes the screening, discovery, and development of appropriate natural genetic sequences for trimerization in the recombinant protein art.

SUMMARY OF THE INVENTION

The present invention relates to a method of preparing a trimeric protein comprising culturing a host cell transformed or transfected with an expression vector encoding a fusion protein comprising a ZymoZipper (ZZ) domain and a heterologous protein. In one embodiment, the heterologous protein is a membrane protein, the portion of the heterologous protein that included in the fusion protein is the extracellular domain of that protein, and the resulting fusion protein is soluble. In another embodiment of the present invention, the ZZ domain is derived from the transmembrane (TM) subunit of a virus envelope protein or another heptad repeat containing gene of a virus genome. In one embodiment, the virus envelope protein is from the Mason-Pfizer Monkey Virus (MPMV). In a further embodiment, the fusion protein comprises a linker sequence. An additional embodiment is where the ZZ domain is derived from the transmembrane (TM) subunit of an endogenous retrovirus, such as a rat endogenous retrovirus (RERV) or a human endogenous retrovirus (HERV), including but not limited to ERVWE1.

A still further embodiment of the present invention is a method of preparing a soluble, hetero-trimeric protein by culturing a host cell transformed or transfected with one expression vector encoding a fusion protein comprising a ZZ domain and a heterologous protein, culturing another host cell transformed or transfected with another expression vector encoding another ZZ domain and a heterologous protein, and culturing a third host cell transformed or transfected with another expression vector encoding yet another ZZ domain and a heterologous protein. In this embodiment, the three ZZ domains preferentially form a hetero-trimer. This culturing can occur in the same host cell. The ZZ domains can be the same or different and the fusion protein can further comprise a linker sequence. In one particular embodiment, the two heterologous proteins used to form the hetero-trimeric protein are the soluble domains of APRIL (a lymphocyte proliferation ligand) and BLyS (B-lymphocyte stimulator). The present invention also encompasses DNA sequences, expression vectors, and transformed host cells utilized in the present method and fusion proteins produced by the present method.

These and other aspects of the invention will become apparent to those persons skilled the art upon reading the details of the invention as more fully described below.

DETAILED DESCRIPTION OF THE INVENTION

Figure 1:
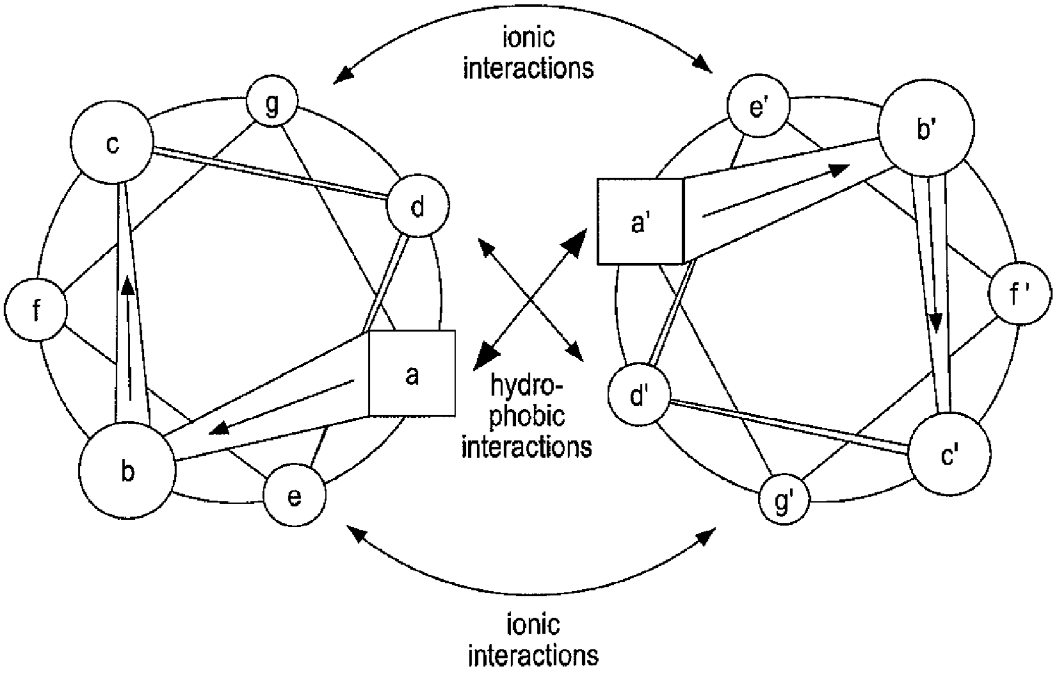
FIG. 1. is a graphic representation of the structure of coiled-coil proteins and the interaction between residues within the coil and the residues between coils.

The present invention provides a method of preparing a trimeric protein by culturing a host cell transformed or transfected with an expression vector encoding a fusion protein comprising a ZymoZipper (ZZ) domain and a heterologous protein. The invention is based on the finding that trimerization sequences derived from the transmembrane TM subunit of certain viruses result in highly bioactive fusion proteins. This observation allowed the development of a fusion protein production method that can be utilized to produce homo- or hetero-trimeric proteins that retain their biological activity.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a polymorphism includes a plurality of such polymorphisms, reference to "a nucleic acid molecule" includes a plurality of such nucleic acid molecules, and reference to "the method" includes reference to one or more methods, method steps, and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

In the present patent application, the term "fusion protein" is used herein to describe a protein whose sequences derive from at least two different gene sources. The sequences are genetically engineered to be transcribed and translated into one protein that comprises sequences from at least two different genes. For the present invention, one gene source is a viral heptad repeat sequence (known as the ZymoZipper or ZZ domain) and the additional gene source or sources are one or more heterologous genes. The fusion protein can also comprise a linker sequence which will generally be located between the ZZ domain and the heterologous protein sequence.

The term "heterologous" is used to describe a polynucleotide or protein that is not naturally encoded or expressed with the viral heptad repeat sequence of the ZZ domain within the viral genome. If the ZZ domain is derived from a human endogenous retrovirus, any gene source outside of the proteins believed to be encoded by viral-derived sequences is considered heterologous. A heterologous protein can be a full length protein or a particular domain of a protein. The heterologous proteins of the present invention encompass both membrane bound proteins and soluble proteins and domains thereof.

The terms "polynucleotide" and "nucleic acid molecule" are used interchangeably herein to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes single-, double-stranded and triple helical molecules. "Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as oligomers or oligos and may be isolated from genes, or chemically synthesized by methods known in the art.

The following are non-limiting embodiments of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A nucleic acid molecule may also comprise modified nucleic acid molecules, such as methylated nucleic acid molecules and nucleic acid molecule analogs. Analogs of purines and pyrimidines are known in the art. Nucleic acids may be naturally occurring, e.g. DNA or RNA, or may be synthetic analogs, as known in the art. Such analogs may be preferred for use as probes because of superior stability under assay conditions. Modifications in the native structure, including alterations in the backbone, sugars or heterocyclic bases, have been shown to increase intracellular stability and binding affinity. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage.

Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity.

Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

A "substantially isolated" or "isolated" polynucleotide is one that is substantially free of the sequences with which it is associated in nature. By substantially free is meant at least 50%, preferably at least 70%, more preferably at least 80%, and even more preferably at least 90% free of the materials with which it is associated in nature. As used herein, an "isolated" polynucleotide also refers to recombinant polynucleotides, which, by virtue of origin or manipulation: (1) are not associated with all or a portion of a polynucleotide with which it is associated in nature, (2) are linked to a polynucleotide other than that to which it is linked in nature, or (3) does not occur in nature.

Hybridization reactions can be performed under conditions of different "stringency". Conditions that increase stringency of a hybridization reaction of widely known and published in the art. See, for example, Sambrook et al. (1989). Examples of relevant conditions include (in order of increasing stringency): incubation temperatures of 25° C., 37° C., 50° C. and 68° C.; buffer concentrations of 10×SSC, 6×SSC, 1×SSC, 0.1×SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or deionized water. Examples of stringent conditions are hybridization and washing at 50° C. or higher and in 0.1×SSC (9 mM NaCl/0.9 mM sodium citrate).

"$T_m$" is the temperature in degrees Celsius at which 50% of a polynucleotide duplex made of complementary strands hydrogen bonded in anti-parallel direction by Watson-Crick base pairing dissociates into single strands under conditions of the experiment. $T_m$ may be predicted according to a standard formula, such as:

where $[X^+]$ is the cation concentration (usually sodium ion, $Na^+$) in mol/L; (% G/C) is the number of G and C residues as a percentage of total residues in the duplex; (% F) is the percent formamide in solution (wt/vol); and L is the number of nucleotides in each strand of the duplex.

Stringent conditions for both DNA/DNA and DNA/RNA hybridization are as described by Sambrook et al. *Molecular Cloning, A Laboratory Manual,* 2nd Ed., Cold Spring Harbor Laboratory Press, Cold Spring Harbor, N.Y., 1989, herein incorporated by reference. For example, see page 7.52 of Sambrook et al.

The term "host cell" includes an individual cell or cell culture which can be or has been a recipient of any recombinant vector(s) or isolated polynucleotide of the invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with a recombinant vector or a polynucleotide of the invention. A host cell which comprises a recombinant vector of the invention is a "recombinant host cell".

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger peptide is commonly cleaved to remove the secretory peptide during transit through the secretory pathway.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag (Grussenmeyer et al., *Proc. Natl. Acad. Sci. USA* 82:7952-4, 1985), substance P, Flag™ peptide (Hopp et al., *Biotechnology* 6:1204-10, 1988), streptavidin binding peptide, or other antigenic epitope or binding domain. See, in general, Ford et al., *Protein Expression and Purification* 2: 95-107, 1991. DNAs encoding affinity tags are available from commercial suppliers (e.g., Pharmacia Biotech, Piscataway, N.J.).

The terms "amino-terminal" (N-terminal) and "carboxyl-terminal" (C-terminal) are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

As used herein, the terms "treatment", "treating", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," and "patient," used interchangeably herein, refer to a mammal, including, but not limited to, murines, simians, humans, mammalian farm animals, mammalian sport animals, and mammalian pets.

The ZymoZipper (ZZ) Domain

The present invention is a method of producing a trimeric protein that comprises a fusion protein comprising a ZZ domain and a herterologous protein domain. ZZ domains are derived from viral heptad repeats as found in the TM subunit of many virus species. Representative virus genus or families having appropriate TM domains or other viral genes including heptad repeats include but are not limited to Orthomyxovirus, Filovirus, Betaretrovirus, Gammaretrovirus, Deltraretrovirus, Lentivirus, Cornaviruses and Paramyoxvirus. One particular Betaretrovirus contemplated for the present invention is the Mason Pfizer Monkey virus (MPMV). Other particular viruses contemplated for the present invention include but are not limited to Influenza virus, Ebola virus, FRMLV, MoMLV, HTLV-1, HIV-1 and SIV. Sequences are selected for their anticipated ability to form coiled-coil protein structure, as this structure is important for the ability to form multimeric protein forms. Particularly desired for the present invention is the ability of coiled-coil proteins to produce trimeric protein structures. Selection of appropriate sequences can involve the utilization of sequence comparison software, such as the BLAST program available from the National Center for Biotechnology Information, as described below in Example 1.

A further potential source of ZZ domain sequences are TM subunits of endogenous retroviruses. This includes endogenous rat, mouse, or human retrovirus (HERV) sequences. Beyond comprising the viral heptad repeats that are characteristic of coiled-coil structure, the proteins of HERVs have been found to be expressed in human tissues. For example, the HERV-W family includes a locus, ERVWE1 that produces a protein known as syncytin. The advantage of working with such sequences as ZZ domains is the anticipated reduced antigenicity that an endogenous sequence would have when introduced into a human subject.

Work with other types of zipper sequences, for examples, the leucine zipper, has shown that a limited number of conservative amino acid substitutions (even at the d residue) can be often be tolerated in zipper sequences without the loss of the ability of the molecules to multimerize (Landschultz et al., (1989), supra;). Thus, conservative changes from the native viral sequence for the ZZ domain are contemplated within the scope of the invention. Table 1 shows the conservative changes that are anticipated to tolerated by the zipper structure.

TABLE 1

Conservative amino acid substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| | methionine |
| Aromatic: | phenylalanine |
| | tryptophan |
| | tyrosine |
| Small: | glycine |
| | alanine |
| | serine |
| | threonine |
| | methionine |

If more than one fusion protein is being used to produce hetero-multimeric proteins, for example, heterotrimers, the ZZ domain that is used can be the same domain for both fusion proteins or different ZZ domains, as long as the domains have the ability to associate with each other and form multimeric proteins.

The ZZ domain can be put at either the N or C terminus of the heterologous protein of interest, based on considerations of function (i.e., whether the heterologous protein is a type I or type II membrane protein) and ease of construction of the construct.

Heterologous Proteins—Proteins of Interest

A heterologous protein of interest is selected primarily based on a desire to produce a multimeric, particularly trimeric, version of the protein. Additionally, by utilizing only a soluble domain of the heterologous protein, a transmembrane protein can be produced in soluble form. Of particular interest with the present invention is the production of biologically active proteins of interest. One family of proteins that commonly utilizes trimers for activity is the tumor necrosis factor (TNF) family. Members of this family include two ligands, APRIL and BLyS. Soluble human APRIL has been made in mammalian cells in several forms: with a Flag tag (Hahne et al. (1998) J Exp Med; 188:1185-1190), as a fusion protein with ACRP30 soluble TNF domain (Rennert et al. (2000) J Exp Med; 192, 1677-1684), or secreted alkaline phosphatase (Marsters et al. (2000) Curr Biol; 10: 785-788). Two amino termini residues 105 and 110 have been published for making the soluble form of APRIL, and both forms include the heparin binding motif (residues 109-114) (Ingold et al. (2005) J Exp Med; 201:1375-1383; Hendriks et al. (2005) Cell Death Differ; 12: 637-648).

Despite the fact that the crystal structure of murine APRIL shows a homotrimeric structure (and soluble human APRIL fused to the Flag epitope has been shown to form a homotrimer as well (unpublished data)), APRIL seems to require a trimeric fusion partner in order to form an active soluble molecule (Rennert et al., supra). Thus, this protein was selected as a representative heterologous protein to express using the ZZ-Heterologous Fusion protein method and production and biological assays of its function are described below in Examples 1-4. Another possible protein that can be produced using the ZZ fusion protein method is BLyS. By utilizing ZZ fusion proteins constructs for both TNF ligands, APRIL and BLyS hetero-trimers may be produced.

Linker Sequences, Affinity Tag Sequences, and Signal Peptides

A protein of interest may be linked directly to another protein to form a a fusion protein; alternatively, the proteins maybe separated by a distance sufficient to ensure the proteins form proper secondary and teriary structure needed for biological activity. Suitable linker sequences will adopt a flexible extended confirmation and will not exhibit a propensity for developing an ordered secondary structure which could interact with the function domains of the fusions proteins, and will have minimal hydrophobic or charged character which could also interfere with the function of fusion domains. Linker sequences should be constructed with the viral hetad repeat in mind, as it may not be in the best interest of producing a biologically active protein to tightly constrict the N or C terminus of the heterologous sequence. This issue is examined experimentally in Example 4, below. Beyond these considerations, the length of the linker sequence may vary without significantly affecting the biological activity of the fusion protein. Linker sequences can be used between any and all components of the fusion protein (or expression construct) including affinity tags and signal peptides.

A further component of the fusion protein can be an affinity tag. Such tags do not alter the biological activity of fusion proteins, are highly antigenic, and provides an epitope that can be reversibly bound by a specific binding molecule, such as a monoclonal antibody, enabling repaid detection and purification of an expressed fusion protein. Affinity tages can also convey resistance to intracellular degradation if proteins are produced in bacteria, like *E. coli*. An exemplary affinity tag is the FLAG Tag (SEQ ID NO: 58). Methods of producing fusion proteins utilizing this affinity tag for purification are described in U.S. Pat. No. 5,011,912.

A still further component of the fusion protein can be a signal sequence or leader sequence. These sequences are generally utilized to allow for secretion of the fusion protein from the host cell during expression and are also known as a leader sequence, prepro sequence or pre sequence. The secretory signal sequence may be that of the heterologous protein being produced, if it has such a sequence, or may be derived from another secreted protein (e.g., t-PA) or synthesized de novo. The secretory signal sequence is operably linked to fusion protein DNA sequence, i.e., the two sequences are joined in the correct reading frame and positioned to direct the newly sythesized polypeptide into the secretory pathway of the host cell. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830). An example of a suitable leader sequence for the present invention is an optimized leader derived from the human tissue plasmogen activator gene (tPA) (SEQ ID NOS: 39 and 40).

Preparation of Polynucleotides Encoding ZZ-Heterologous Fusion Proteins

The nucleic acid compositions of the present invention find use in the preparation of all or a portion of the ZZ-Heterologous fusion proteins, as described above. The subject polynucleotides (including cDNA or the full-length gene) can be used to express a partial or complete gene product. Constructs comprising the subject polynucleotides can be generated synthetically. Alternatively, single-step assembly of a gene and entire plasmid from large numbers of oligodeoxyribonucleotides is described by, e.g., Stemmer et al., *Gene* (*Amsterdam*) (1995) 164(1):49-53. In this method, assembly PCR (the synthesis of long DNA sequences from large numbers of oligodeoxyribonucleotides (oligos)) is described. The method is derived from DNA shuffling (Stemmer, *Nature* (1994) 370:389-391), and does not rely on DNA ligase, but instead relies on DNA polymerase to build increasingly longer DNA fragments during the assembly process. Appropriate polynucleotide constructs are purified using standard recombinant DNA techniques as described in, for example, Sambrook et al., *Molecular Cloning: A Laboratory Manual,* 2nd Ed., (1989) Cold Spring Harbor Press, Cold Spring Harbor, N.Y., and under current regulations described in United States Dept. of HHS, National Institute of Health (NIH) Guidelines for Recombinant DNA Research.

Polynucleotide molecules comprising a polynucleotide sequence provided herein are propagated by placing the molecule in a vector. Viral and non-viral vectors are used, including plasmids. The choice of plasmid will depend on the type of cell in which propagation is desired and the purpose of propagation. Certain vectors are useful for amplifying and making large amounts of the desired DNA sequence. Other vectors are suitable for expression in cells in culture. Still other vectors are suitable for transfer and expression in cells in a whole animal or person. The choice of appropriate vector is well within the skill of the art. Many such vectors are available commercially. The partial or full-length polynucleotide is inserted into a vector typically by means of DNA ligase attachment to a cleaved restriction enzyme site in the vector. Alternatively, the desired nucleotide sequence can be inserted by homologous recombination in vivo. Typically this is accomplished by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example.

For expression, an expression cassette or system may be employed. The gene product encoded by a polynucleotide of the invention is expressed in any convenient expression system, including, for example, bacterial, yeast, insect, amphibian and mammalian systems. Suitable vectors and host cells are described in U.S. Pat. No. 5,654,173. In the expression vector, an polymorphic BLyS polypeptide-encoding polynucleotide is linked to a regulatory sequence as appropriate to obtain the desired expression properties. These-can include promoters (attached either at the 5' end of the sense strand or at the 3' end of the antisense strand), enhancers, terminators, operators, repressors, and inducers. The promoters can be regulated or constitutive. In some situations it may be desirable to use conditionally active promoters, such as tissue-specific or developmental stage-specific promoters. These are linked to the desired nucleotide sequence using the techniques described above for linkage to vectors. Any techniques known in the art can be used. In other words, the expression vector will provide a transcriptional and translational initiation region, which may be inducible or constitutive, where the coding region is operably linked under the transcriptional control of the transcriptional initiation region, and a transcriptional and translational termination region. These control regions may be native to the DNA encoding the ZZ-heterologous fusion protein, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for the production of fusion proteins, where the exogenous fusion peptide provides additional functionality, i.e. increased protein synthesis, stability, reactivity with defined antisera, an enzyme marker, e.g. β-galactosidase, etc.

Expression cassettes may be prepared comprising a transcription initiation region, the gene or fragment thereof, and a transcriptional termination region. Of particular interest is the use of sequences that allow for the expression of functional epitopes or domains, usually at least about 8 amino acids in length, more usually at least about 15 amino acids in length, to about 25 amino acids, and up to the complete open reading frame of the gene. After introduction of the DNA, the cells containing the construct may be selected by means of a selectable marker, the cells expanded and then used for expression.

ZZ-Heterologous fusion proteins may be expressed in prokaryotes or eukaryotes in accordance with conventional ways, depending upon the purpose for expression. For large scale production of the protein, a unicellular organism, such as *E. coli*, *B. subtilis*, *S. cerevisiae*, insect cells in combination with baculovirus vectors, or cells of a higher organism such as vertebrates, particularly mammals, e.g. COS 7 cells, HEK 293, CHO, *Xenopus* Oocytes, etc., may be used as the expression host cells. In some situations, it is desirable to express a polymorphic BLyS nucleic acid molecule in eukaryotic cells, where the polymorphic BLyS protein will benefit from native folding and post-translational modifications. Small peptides can also be synthesized in the laboratory. Polypeptides that are subsets of the complete BLyS sequence may be used to identify and investigate parts of the protein important for function.

Specific expression systems of interest include bacterial, yeast, insect cell and mammalian cell derived expression systems. Representative systems from each of these categories is are provided below:

Bacteria. Expression systems in bacteria include those described in Chang et al., *Nature* (1978) 275:615; Goeddel et al., *Nature* (1979) 281:544; Goeddel et al., *Nucleic Acids Res.* (1980) 8:4057; EP 0 036,776; U.S. Pat. No. 4,551,433; DeBoer et al., *Proc. Natl. Acad. Sci.* (*USA*) (1983) 80:21-25; and Siebenlist et al., *Cell* (1980) 20:269.

Yeast. Expression systems in yeast include those described in Hinnen et al., *Proc. Natl. Acad. Sci.* (USA) (1978) 75:1929; Ito et al., *J. Bacteriol.* (1983) 153:163; Kurtz et al., *Mol. Cell. Biol.* (1986) 6:142; Kunze et al., *J. Basic Microbiol.* (1985) 25:141; Gleeson et al., *J. Gen. Microbiol.* (1986) 132:3459; Roggenkamp et al., *Mol. Gen. Genet.* (1986) 202:302; Das et al., *J. Bacteriol.* (1984) 158:1165; De Louvencourt et al., *J. Bacteriol.* (1983) 154:737; Van den Berg et al., *Bio/Technology* (1990) 8:135; Kunze et al., *J. Basic Microbiol.* (1985) 25:141; Cregg et al., *Mol. Cell. Biol.* (1985) 5:3376; U.S. Pat. Nos. 4,837,148 and 4,929,555; Beach and Nurse, *Nature* (1981) 300:706; Davidow et al., *Curr. Genet.* (1985) 10:380; Gaillardin et al., *Curr. Genet.* (1985) 10:49; Ballance et al., *Biochem. Biophys. Res. Commun.* (1983) 112:284-289; Tilburn et al., *Gene* (1983) 26:205-221; Yelton et al., *Proc. Natl. Acad. Sci.* (*USA*) (1984) 81:1470-1474; Kelly and Hynes, *EMBO J.* (1985) 4:475-479; EP 0 244,234; and WO 91/00357.

Insect Cells. Expression of heterologous genes in insects is accomplished as described in U.S. Pat. No. 4,745,051; Friesen et al., "The Regulation of Baculovirus Gene Expression", in: *The Molecular Biology Of Baculoviruses* (1986) (W. Doerfler, ed.); EP 0 127,839; EP 0 155,476; and Vlak et al., *J. Gen. Virol.* (1988) 69:765-776; Miller et al., *Ann. Rev. Microbiol.* (1988) 42:177; Carbonell et al., *Gene* (1988) 73:409; Maeda et al., *Nature* (1985) 315:592-594; Lebacq-Verheyden et al., *Mol. Cell. Biol.* (1988) 8:3129; Smith et al., *Proc. Natl. Acad. Sci.* (*USA*) (1985) 82:8844; Miyajima et al., *Gene* (1987) 58:273; and Martin et al., *DNA* (1988) 7:99. Numerous baculoviral strains and variants and corresponding permissive insect host cells from hosts are described in Luckow et al., *Bio/Technology* (1988) 6:47-55, Miller et al., *Generic Engineering* (1986) 8:277-279, and Maeda et al., *Nature* (1985) 315:592-594.

Mammalian Cells. Mammalian expression is accomplished as described in Dijkema et al., *EMBO J.* (1985) 4:761, Gorman et al., *Proc. Natl. Acad. Sci.* (*USA*) (1982) 79:6777, Boshart et al., *Cell* (1985) 41:521 and U.S. Pat. No. 4,399,216. Other features of mammalian expression are facilitated as described in Ham and Wallace, *Meth. Enz.* (1979) 58:44, Barnes and Sato, *Anal. Biochem.* (1980) 102:255, U.S. Pat. Nos. 4,767,704, 4,657,866, 4,927,762, 4,560,655, WO 90/103430, WO 87/00195, and U.S. Pat. No. RE 30,985.

When any of the above host cells, or other appropriate host cells or organisms, are used to replicate and/or express the polynucleotides or nucleic acids of the invention, the resulting replicated nucleic acid, RNA, expressed protein or polypeptide, is within the scope of the invention as a product of the host cell or organism. The product is recovered by any appropriate means known in the art.

Once the gene corresponding to a selected polynucleotide is identified, its expression can be regulated-in the cell to which the gene is native. For example, an endogenous gene of a cell can be regulated by an exogenous regulatory sequence inserted into the genome of the cell at location sufficient to at least enhance expressed of the gene in the cell. The regulatory sequence may be designed to integrate into the genome via homologous recombination, as disclosed in U.S. Pat. Nos. 5,641,670 and 5,733,761, the disclosures of which are herein incorporated by reference, or may be designed to integrate into the genome via non-homologous recombination, as described in WO 99/15650, the disclosure of which is herein incorporated by reference.

Vectors and Host Cells Comprising the Polynucleotides of the Invention

The invention further provides recombinant vectors and host cells comprising polynucleotides of the invention. In general, recombinant vectors and host cells of the invention are isolated; however, a host cell comprising a polynucleotide of the invention may be part of a genetically modified animal.

Recombinant vectors. The present invention further provides recombinant vectors ("constructs") comprising a polynucleotide of the invention. Recombinant vectors include vectors used for propagation of a polynucleotide of the invention, and expression vectors. Vectors useful for introduction of the polynucleotide include plasmids and viral vectors, e.g. retroviral-based vectors, adenovirus vectors, etc. that are maintained transiently or stably in mammalian cells. A wide variety of vectors can be employed for transfection and/or integration of the gene into the genome of the cells. Alternatively, micro-injection may be employed, fusion, or the like for introduction of genes into a suitable host cell.

Expression vectors generally have convenient restriction sites located near the promoter sequence to provide for the insertion of nucleic acid sequences encoding heterologous proteins. A selectable marker operative in the expression host may be present. Expression vectors may be used for the production of fusion proteins, where the exogenous fusion peptide provides additional functionality, i.e. increased protein synthesis, stability, reactivity with defined antisera, an enzyme marker, e.g. β-galactosidase, etc.

Expression cassettes may be prepared comprising a transcription initiation region, the gene or fragment thereof, and a transcriptional termination region. Of particular interest is the use of sequences that allow for the expression of functional epitopes or domains, usually at least about 8 amino acids in length, more usually at least about 15 amino acids in length, at least about 25 amino acids, at least about 45 amino acids, and up to the complete open reading frame of the gene. After introduction of the DNA, the cells containing the construct may be selected by means of a selectable marker, the cells expanded and then used for expression.

The expression cassettes may be introduced into a variety of vectors, e.g. plasmid, BAC, YAC, bacteriophage such as lambda, P1, M13, etc., animal or plant viruses, and the like, where the vectors are normally characterized by the ability to provide selection of cells comprising the expression vectors. The vectors may provide for extrachromosomal maintenance, particularly as plasmids or viruses, or for integration into the host chromosome. Where extrachromosomal maintenance is desired, an origin sequence is provided for the replication of the plasmid, which may be low- or high copy-number. A wide variety of markers are available for selection, particularly those which protect against toxins, more particularly against antibiotics. The particular marker that is chosen is selected in accordance with the nature of the host, where in some cases, complementation may be employed with auxotrophic hosts. Introduction of the DNA construct may use any convenient method, e.g. conjugation, bacterial transformation, calcium-precipitated DNA, electroporation, fusion, transfection, infection with viral vectors, biolistics, etc.

Genetically Modified Cells. The present invention further provides host cells, which may be isolated host cells, comprising polymorphic BLyS nucleic acid molecules of the invention. Suitable host cells include prokaryotes such as *E. coli, B. subtilis*, eukaryotes, including insect cells in combination with baculovirus vectors, yeast cells, such as *Saccharomyces cerevisiae*, or cells of a higher organism such as vertebrates, including amphibians (e.g., *Xenopus laevis* oocytes), and mammals, particularly humans, e.g. COS cells, CHO cells, HEK293 cells, and the like, may be used as the host cells. Host cells can be used for the purposes of propagating a polymorphic BLyS nucleic acid molecule, for production of a polymorphic BLyS polypeptide, or in cell-based methods for identifying agents which modulate a level of BLyS mRNA and/or protein and/or biological activity in a cell.

Primary or cloned cells and cell lines may be modified by the introduction of vectors comprising a DNA encoding the ZZ-heterologous fusion protein polymorphism(s). The isolated polymorphic BLyS nucleic acid molecule may comprise one or more variant sequences, e.g., a haplotype of commonly occurring combinations. In one embodiment of the invention, a panel of two or more genetically modified cell lines, each cell line comprising a BLyS polymorphism, are provided for substrate and/or expression assays. The panel may further comprise cells genetically modified with other genetic sequences, including polymorphisms, particularly other sequences of interest for pharmacogenetic screening, e.g. other genes/gene mutations associated with obesity, a number of which are known in the art.

Transgenic animals. The subject nucleic acids can be used to generate genetically modified non-human animals or site specific gene modifications in cell lines. The term "transgenic" is intended to encompass genetically modified animals having the addition of DNA encoding the ZZ-heterologous fusion protein or having an exogenous DNA encoding the ZZ-heterologous fusion protein that is stably transmitted in the host cells. Transgenic animals may be made through homologous recombination. Alternatively, a nucleic acid construct is randomly integrated into the genome. Vectors for stable integration include plasmids, retroviruses and other animal viruses, YACs, and the like. Of interest are transgenic mammals, e.g. cows, pigs, goats, horses, etc., and particularly rodents, e.g. rats, mice, etc.

DNA constructs for homologous recombination will comprise at least a portion of the DNA encoding the ZZ-heterologous fusion protein and will include regions of homology to the target locus. Conveniently, markers for positive and negative selection are included. Methods for generating cells having targeted gene modifications through homologous recombination are known in the-art. For various techniques for transfecting mammalian cells, see Known et al. (1990) *Methods in Enzymology* 185:527-537.

For embryonic stem (ES) cells, an ES cell line may be employed, or ES cells may be obtained freshly from a host, e.g. mouse, rat, guinea pig, etc. Such cells are grown on an appropriate fibroblast-feeder layer or grown in the presence of leukemia inhibiting factor (LIF). When ES cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination. Those colonies that show homologous recombination may then be used for embryo manipulation and blastocyst injection. Blastocysts are obtained from. 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for mutant cells having the construct. By providing for a different phenotype of the blastocyst and the ES cells, chimeric progeny can be readily detected. The chimeric animals are screened for the presence of the DNA encoding the ZZ-heterologous fusion protein and males and females having the modification are mated to produce homozygous progeny. The transgenic animals may be any non-human mammal, such as laboratory animals, domestic animals, etc. The transgenic animals may be used to determine the effect of a candidate drug in an in vivo environment.

Production of Hetero-Trimeric Proteins Utilizing ZZ Constructs

The present invention is a method of preparing a soluble, hetero-trimeric protein by culturing a host cell transformed or transfected with one expression vector encoding a fusion protein comprising a ZZ domain and a heterologous protein, culturing another host cell transformed or transfected with another expression vector encoding another ZZ domain and a heterologous protein, and culturing a third host cell transformed or transfected with another expression vector encoding yet another ZZ domain and a heterologous protein. In order to produce a biologically functioning protein, the three ZZ domains preferentially form a hetero-trimer. The culturing can also occur in the same host cell, if efficient production can be maintained, and hetero-trimeric proteins are then isolated from the medium. Ideally, the three heterologous proteins are differentially labeled with various tag sequences (i.e., His tag, FLAG tag, and Glu-Glu tag) to allow analysis of the composition or purification of the resulting molecules. Alternatively, the three components can be produced separately and combined in deliberate ratios to result in the hetero-trimeric molecules desired. The ZZ domains utilized in making these hetero-trimeric molecules can be the same or different and the fusion protein(s) can further comprise a linker sequence. In one particular embodiment, the two heterologous proteins used to form the hetero-trimeric protein are the soluble domains of APRIL (a lymphocyte proliferation ligand) and BLyS (B-lymphocyte stimulator).

Biological Activity of the ZZ-Heterologous Fusion Proteins

Biological activity of recombinant ZZ-heterologous fusion proteins is mediated by binding of the recombinant fusion protein to a cognate molecule, such as a receptor. A cognate molecule is defined as a molecule which binds the recombinant fusion protein in a non-covalent interaction based upon the proper conformation of the recombinant fusion protein and the cognate molecule. For example, for a recombinant fusion protein comprising an extracellular region of a receptor, the cognate molecule comprises a ligand which binds the extracellular region of the receptor. Conversely, for a recombinant soluble fusion protein comprising a ligand, the cognate molecule comprises a receptor (or binding protein) which binds the ligand.

Binding of a recombinant fusion protein to a cognate molecule is a marker for biological activity. Such binding activity may be determined, for example, by competition for binding to the binding domain of the cognate molecule (i.e. competitive binding assays). One configuration of a competitive binding assay for a recombinant fusion protein comprising a ligand uses a radiolabeled, soluble receptor, and intact cells expressing a native form of the ligand. Similarly, a competitive assay for a recombinant fusion protein comprising a receptor uses a radiolabeled, soluble ligand, and intact cells expressing a native form of the receptor. Such an assay is described in Example 5. Instead of intact cells expressing a native form of the cognate molecule, one could substitute purified cognate molecule bound to a solid phase. Competitive binding assays can be performed using standard methodology. Qualitative or semi-quantitative results can be obtained by competitive autoradiographic plate binding assays, or fluorescence activated cell sorting, or Scatchard plots may be utilized to generate quantitative results.

Biological activity may also be measured using bioassays that are known in the art, such as a cell proliferation assay. Exemplary bioassays are described in Examples 5 and 6 herein. The type of cell proliferation assay used will depend upon the recombinant soluble fusion protein. A bioassay for a recombinant soluble fusion protein that in its native form acts upon T cells will utilize purified T cells obtained by methods that are known in the art. Such bioassays include costimulation assays in which the purified T cells are incubated in the presence of the recombinant soluble fusion protein and a suboptimal level of a mitogen such as Con A or PHA. Similarly, purified B cells will be used for a recombinant soluble fusion protein that in its native form acts upon B cells. Other types of cells may also be selected based upon the cell type upon which the native form of the recombinant soluble fusion protein acts. Proliferation is determined by measuring the incorporation of a radiolabeled substance, such as $^3$H thymidine, according to standard methods.

Yet another type assay for determining biological activity is induction of secretion of secondary molecules. For example, certain proteins induce secretion of cytokines by T cells. T cells are purified and stimulated with a recombinant soluble fusion protein under the conditions required to induce cytokine secretion (for example, in the presence of a comitogen). Induction of cytokine secretion is determined by bioassay, measuring the proliferation of a cytokine dependent cell line. Similarly, induction of immunoglobulin secretion is determined by measuring the amount of immunoglobulin secreted by purified B cells stimulated with a recombinant soluble fusion protein that acts on B cells in its native form, using a quantitative (or semi-quantitative) assay such as an enzyme immunoassay.

Treatment Methods

For pharmaceutical use, the fusion proteins of the present invention are formulated for parenteral, particularly intravenous or subcutaneous, administration according to conventional methods. Intravenous administration will be by bolus injection or infusion over a typical period of one to several hours. In general, pharmaceutical formulations will include a ZZ-heterologous fusion protein in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in *Remington's Pharmaceutical Sciences*, Gennaro, ed., Mack Publishing Co., Easton Pa., 1990, which is incorporated herein by reference. Therapeutic doses will generally be in the range of 0.1 to 100 μg/kg of patient weight per day, preferably 0.5-20 μg/kg per day, with the exact dose determined by the clinician according to accepted standards, taking into account the nature and severity of the condition to be treated, patient traits, etc. Determination of dose is within the level of ordinary skill in the art. The proteins may be administered for acute treatment, over one week or less, often over a period of one to three days or may be used in chronic treatment, over several months or years. In general, a therapeutically effective amount of ZZ-heterologous fusion protein is an amount sufficient to produce a clinically significant change in the symptoms characteristics of the lack of heterologous protein function. Alternatively, if the ZZ-heterologous fusion protein is to act as an antagonist, a therapeutically effective amount is that which produces a clinically significant change in symptoms characteristic of an over-abundance of heterologous protein function.

Enzymatic Removal of the ZZ-Domain

Depending on the intended use of the ZZ-heterologous fusion protein, it can be advantageous to remove the ZZ-domain after protein production but prior to the final use of the protein. The removal of this domain can be accomplished using proteases well known to one of ordinary skill. The target sequence specific for cleavage by various proteases is well known, and such sequences can be present in the ZymoZipper sequence itself naturally or through genetic engineering. Preferably, in order to avoid changes in the multimerizing function of the ZZ-domain, the target sequence can be found or engineered into another portion of the fusion protein, such as the linker region. Some enzymes appropriate for this removal process include, but are not limited to trypsin, Lys C, Lys N, Arg C, Asp N, Glu C (bicarbonate or phosphate conditions), chymotrypsin, pepsin (at various pH ranges), proteinase K, and papain. Combinations of these enzymes can also be used, if necessary, to optimize the removal of the ZZ-domain from the final fusion protein produced.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

Example 1

Selection of Candidate ZZ Sequences

A series of retroviral env sequences were obtained by the Basic Local Alignment Search Tool (BLAST; National Center for Biotechnology Information (NCBI)) using the Moloney murine leukemia envelope TM subunit as a search sequence. This program finds regions of local similarity between sequences and calculates the statistical significance of the matches. BLAST can be used to infer function and evolutionary relationship between sequences as well as help identify member of gene families. The resulting sequences were arranged into a genomic tree and six sequences were selected from different clusters within the collection to maximize the diversity of the heptad sequences assayed. The heptad repeat sequences shown in Table 2 were chosen and used to make fusion proteins with a candidate protein.

TABLE 2

| Heptad component | fg | abcdefg | abcdefg | abcdefg | abcdefg | abcde |
|---|---|---|---|---|---|---|
| ZZ03 (SEQ ID NO: 27) | KE | LREVEKS | IENLNKK | MEDGFLD | VLQNRRG | ----- |
| ZZ07 (SEQ ID NO: 28) | DD | LREVEKS | ISNLEKS | LTSLSEV | VLQNRRG | LDLLF |
| ZZ09 (SEQ ID NO: 29) | DD | LGALEKS | VSALEKS | LTSLSEV | VLQNRRG | LDLLF |
| ZZ10 (SEQ ID NO: 30) | AD | VQRLQQG | VDDLSDS | LSSLAEV | VLQNRRG | LDLLF |
| ZZ11 (SEQ ID NO: 31) | NG | FRKMSQT | MLTIQKQ | IDSLAAV | VLQNRRG | LDVLT |
| ZZ12 (SEQ ID NO: 32) | SD | VQAISSTI | QDLQDQ | VDSLAEV | VLQNRRG | LDLLT |

Because of the difficulties in producing biologically active APRIL, this protein was selected to produce a fusion protein. Proteins were engineered to include a signal peptide, a Flag tag, the ZZ sequence, a linker, and amino acids 110-250 of APRIL.

Example 2

Construction of ZZ Expression Vectors

Primers for each of the ZZ constructs were organized as follows: two halves, front (F) and back (B), each half composed of two primers, 5' and 3'. The F and B halves were assembled from their respective 5' and 3' primers by PCR as described below and disclosed in Table 3, then aliquots of F and B for each ZZ were assembled into each full ZZ sequence by overlap PCR with primers zc49141 and zc49142. PCR conditions were as follows: 1 cycle, 94° C., 2 minutes; 35 cycles, 94° C., 30 seconds, followed by 55° C., 30 seconds, followed by 72° C., 30 seconds; 1 cycle, 72° C., 5 minutes. Ten percent of each of the PCR reaction mixtures were run on a 1.8% agarose gel for analysis. The remaining portion of the PCR fragments were precipitated by the addition of 10 μL 3M Na Acetate and 250 μL ethanol, centrifuged at 13,000×g 30 minutes, the pellet rinsed once with 70% ethanol and allowed to dry in air. The pellets were resuspended in 10 μL of distilled water.

These PCR resulted in a series of products (228-246 bp) consisting of each ZZ sequence (ZZ3, ZZ7, ZZ9, ZZ10, ZZ11, ZZ12) with 40 by of flanking sequence on either end to promote homologous recombination into the proper site at the amino terminal end of APRIL. These were inserted into an expression vector consisting of pZMP21 with APRIL [res#110-250], the optimized tPA leader, and a sequence that confers trimerizing properties. The vector pZMP21 is a mammalian expression vector described in patent pub. No. US2003/023414 A1 and deposited at the American Type Culture Collection, 10801 University Boulevard, Manassas, Va. 20110-2209 (designated ATCC #PTA-5266). The APRIL vector was linearized at a unique Bgl II site at the intended site of recombination and the trimerizing sequence was replaced by ZZ sequences using homologous recombination in *Saccharomyces cerevisieae.*

The recombination was performed as follows: 100 µL of competent yeast cells (*S. cerevisiae*) were combined with 10 µl of the mixture of PCR product and linearized vector then transferred to a 0.2 cm electroporation cuvette. The yeast/DNA mixtures were electropulsed at 0.75 kV (5 kV/cm), ∞ oohms, 25 µF. To each cuvette was added 600 µl of 1.2 M sorbitol and the yeast were plated in two 300 µl aliquots onto two URA-D plates and incubated at 30° C. This was done for each ZZ sequence and with linearized vector alone. After about 48 hours, the colonies are evaluated against the vector alone control and the URA+ yeast transformants from positive plates corresponding to each ZZ sequence were resuspended in 1 ml $H_2O$ and spun briefly to pellet the yeast cells. The cell pellet were resuspended in 1 ml of Qiagen buffer P1. Five hundred microliters of each mixture was added to an Eppendorf tube containing 300 µl acid washed glass beads, vortexed for 1 minute intervals two or three times, followed by a 15 second spin in a Eppendorf centrifuge at maximum speed. Three hundred microliters of yeast lysate was transferred to a fresh tube, and the manufacturer's procedure for Qiagen miniprep was followed from that point on. The eluate from QiaPrep columns were precipitated by the addition of 0.1 volume of 3M NaAc and 2.5 volumes of absolute ethanol and DNA pellet was resuspended in 10 µl $H_2O$.

Transformation of electrocompetent *E. coil* cells (DH10B, GibcoBRL) was done with 0.5-2 µl yeast DNA prep and 40 µl of DH10B cells. The cells were electropulsed at 1.7 kV, 25 µF and 400 ohms. Following electroporation, 1 ml SOC (2% Bacto'Tryptone (Difco, Detroit, Mich.), 0.5% yeast extract (Difco), 10 mM NaCl, 2.5 mM KCl, 10 mM MgCl2, 10 mM MgSO4, 20 mM glucose) was plated in 250 µl aliquots on four LB AMP plates (LB broth (Lennox), 1.8% Bacto Agar (Difco), 100 mg/L Ampicillin). Each completed construct was subjected to sequence analysis and the construct containing the correct sequence was selected for scaleup by QIAGEN Plasmid Mega kit.

TABLE 3

| Primer sequences | | |
|---|---|---|
| oligo | name | Sequence |
| zc49141 | 5' all | AGCCAGGAAATCCATGCCGAGTTGAGACGCTT CCGTAGAGATTATAAGGACGATGACGAT (SEQ ID NO: 1) |
| zc49142 | 3' all | GGTGGCGTTAATGGGAACCAGGTGCAGGACAG AGTGCTGCTTCTTCTGTTTCAGATCTCC (SEQ ID NO: 2) |
| zc49317 | ZZ3 F5' | GATTATAAGGACGATGACGATAAGGGCGGAGG TGGCTCAAAGGAGTTTAACAAC (SEQ ID NO: 3) |
| zc49363 | ZZ3 F3' | CATCTTCTTGTTCAGGTTCTCGATGCGGCGCT CCAGGTTGTTAAACTCCTTTGAGCC (SEQ ID NO: 4) |
| zc49244 | ZZ3 B5' | GAGAACCTGAACAAGAAGATGGAGGACGGTTT TCTGGACGTGTGGACCTAC (SEQ ID NO: 5) |
| zc49310 | ZZ3 B3' | CTTCTTCTGTTTCAGATCTCCCTCGGCGTTGT AGGTCCACACGTCCAGAAA (SEQ ID NO: 6) |

TABLE 3-continued

| Primer sequences | | |
|---|---|---|
| oligo | name | Sequence |
| zc49169 | ZZ7 F5' | GATTATAAGGACGATGACGATAAGGGCGGAGG TGGCTCAGATGATCTGCGCGAGGTG (SEQ ID NO: 7) |
| zc49170 | ZZ7 F3' | GGTCAGGGACTTCTCCAGATTGGAGATGGACT TCTCCACCTCGCGCAGATCATCTGA (SEQ ID NO: 8) |
| zc49171 | ZZ7 B5' | AATCTGGAGAAGTCCCTGACCTCCCTGTCCGA GGTGGTGCTCCAGAACCGCCGCGGC (SEQ ID NO: 9) |
| zc49172 | ZZ7 B3' | CTTCTTCTGTTTCAGATCTCCGAACAGCAGGT CCAGGCCGCGGCGGTTCTGGAGCAC (SEQ ID NO: 10) |
| zc49223 | ZZ9 F5' | GATTATAAGGACGATGACGATAAGGGCGGAGG TGGCTCAGATGATCTGGGCGCCCTG (SEQ ID: 11) |
| zc49224 | ZZ9 F3' | GGTCAGGGACTTCTCCAGGGCGGACACGGATT TTTCCAGGGCGCCCAGATCATCTGA (SEQ ID NO: 12) |
| zc49225 | ZZ9 B5' | GCCCTGGAGAAGTCCCTGACCTCCCTTTCCGA GGTCGTCCTGCAGAACCGCCGCGGC (SEQ ID NO: 13) |
| zc49226 | ZZ9 B3' | CTTCTTCTGTTTCAGATCTCCAAAAAGAAGGT CAAGGCCGCGGCGGTTCTGCAGGAC (SEQ ID NO: 14) |
| zc49227 | ZZ10 F5' | GATTATAAGGACGATGACGATAAGGGCGGAGG TGGCTCAGCCGACGTCCAGCGCCTC (SEQ ID NO: 15) |
| zc49228 | ZZ10 F3' | GGAAAGGGAGTCGGAAAGATCATCGACGCCCT GCTGGAGGCGCTGGACGTCGGC (SEQ ID NO: 16) |
| zc49229 | ZZ10 B5' | GATCTTTCCGACTCCCTTTCCTCCCTCGCCGA GGTGGTGCTGCAGAATCGCCGCGGC (SEQ ID NO: 17) |
| zc49230 | ZZ10 B3' | CTTCTTCTGTTTCAGATCTCCGAAAAGAAGAT CAAGGCCGCGGCGATTCTGCAGCAC (SEQ ID NO: 18) |
| zc49231 | ZZ11 F5' | GATTATAAGGACGATGACGATAAGGGCGGAGG TGGCTCAAATGGCTTTCGCAAGATG (SEQ ID NO: 19) |
| zc49232 | ZZ11 F3' | ATCGATCTGTTTCTGGATCGTAAGCATGGTCT GGGACATCTTGCGAAAGCCATTTGA (SEQ ID NO:20) |
| zc49233 | ZZ11 B5' | ACGATCCAGAAACAGATCGATTCCCTTGCCGC CGTGGTGCTTCAGAATCGCCGCGGC (SEQ ID NO: 21) |
| zc49234 | ZZ11 B3' | CTTCTTCTGTTTCAGATCTCCCGTGAGGACGT CGAGGCCGCGGCGATTCTGAAGCAC (SEQ ID NO: 22) |
| zc49235 | ZZ12 F5' | GATTATAAGGACGATGACGATAAGGGCGGAGG TGGCTCATCCGACGTCCAGGCGATC (SEQ ID NO: 23) |
| zc49236 | ZZ12 F3' | GTCGACCTGGTCCTGAAGGTCCTGGATGGTGG AGGAGATCGCCTGGACGTCGGATGA (SEQ ID NO: 24) |
| zc49237 | ZZ12 B5' | GACCTTCAGGACCAGGTCGACTCCCTGGCGGA GGTGGTGCTGCAGAATCGCCGCGGC (SEQ ID NO: 25) |

TABLE 3-continued

| Primer sequences | | |
|---|---|---|
| oligo | name | Sequence |
| zc49238 | ZZ12 B3' | CTTCTTCTGTTTCAGATCTCCCGTAAGAAGGT CAAGGCCGCGGCGATTCTGCAGCAC (SEQ ID NO: 26) |

Example 3

Expression of ZZ-APRIL Panel in 293F and Cho Cells and Purification

Transient Expression in 293F Cells

The ZZ-APRIL constructs were first expressed transiently in 293F cells so protein could be produced to test for biological activity. The transient expression was achieved using a high through-put method that achieves the following reagent parameters: Lipid/DNA ratio of 1.33 mg/mg; DNA per transfection of 1500 μg; total transfection volume of 1500 ml; lipid per transfection of 2000 μl; number of transfections of 15; OpitMEM per transfection of 40 ml.

The transfection protocol was as follows: 1000 ml of 293F cells were seeded in a 3 L spinner flask at 435 c/mL 72 hrs prior to transfection. Cells were cultured in a phone-booth incubator at 37° C., 6% $CO_2$, at 95 RPM. The cells were then diluted to 136 c/ml in 1500 ml immediately before transfection. The DNA/Lipid complex was prepared by diluting 2 ml of lipofectamine 2000 in 20 ml of OptiMEM (Invitrogen (Gibco), Carlsbad, Calif.). Next, 1.5 mg of ZZ construct DNA was diluted in 20 ml of OptiMEM. These two solutions are incubated for 5 minutes at room temperature, then combined and incubated for 20-30 minutes at room temperature, inverting occasionally. The DNA/Lipid mixture is then added to the spinner flask. The transfected cells are incubated in a phone booth incubator at 37° C., 6% $CO_2$, at 75 RPM. Supernatant is harvested 96 hours post-transfection.

Expression in CHO Cells 1.5 mg of the ZZ constructs were each digested using various restriction enzymes at 37° C. for three hours and then were precipitated with IPA and spun down in a 1.5 mL microfuge tube. The supernatant was decanted off the pellet, and the pellet was washed with 1 mL of 70% ethanol and allowed to incubate for 5 minutes at room temperature. The tube was spun in a microfuge for 10 minutes at 14,000 RPM and the supernatant was decanted off the pellet. The pellet was then resuspended in 750 μl of PF-CHO media in a sterile environment, allowed to incubate at 60° C. for 30 minutes, and was allowed to cool to room temperature. 5E6 APFDXB11 cells were spun down in one 15 mL conical tube for each ZZ construct and were resuspended using the DNA-media solution. The DNA/cell mixtures were placed in a 0.4 cm gap cuvette and electroporated using the following parameters: 950 μF, high capacitance, and 300V. The contents of the cuvettes were then removed and diluted to 25 mLs with PF-CHO media and placed in a 125 mL shake flask. The flask was placed in an incubator on a shaker at 37° C., 6% $CO_2$, and shaking at 120 RPM.

The cell lines were subjected to nutrient selection followed amplification at 500 nM Methotrexate (MTX). Expression was confirmed by western blot, and the cell line was scaled-up and protein purification followed.

Purification Scheme for ZZ-APRIL NF

All procedures performed at 4 C.° unless otherwise noted. The conditioned media produced from either transient 293F cell expression or CHO cell expression was directly loaded onto a BIO-RAD Macro-Prep Ceramic Hydroxyapatite 80 uM column. The column was washed with 0.2 M PO4, pH 6.8 and eluted with a 10CV gradient from 0.2 M PO4, pH 6.8 to 0.4 M PO4, pH 6.8. The elution step was performed at ambient temperature.

NuPAGE gels (coomassie stained), western and RP-HPLC were performed to analyze the elution. Fractions of interest were pooled and further purified on an anti-flag M2 Affinity column (Kodak). For some fusion proteins, this step is better accomplished using a cation column. The column was equilibrated and washed with PBS, pH 7.3. The column was then eluted with 10 mM PO4, 40 mM Citrate, 100 mM AmSO4, pH 3.0. Fractions were neutralized with 2 M Tris, pH 8.0.

The anti-flag pool (or cation column pool) was concentrated using a Amicon Ultra centrifugal device, 30,000 mwco and loaded onto an equilibrated (GE Healthcare) Superdex 200. The buffer used was 50 mM PO4, 250 mM NaCl, pH 6.8.

Fractions were pooled based on results from NuPAGE gels (coomassie stained), westerns and RP-HPLC.

Western and coomassie stained NuPAGE gels were performed on the pool to confirm purity and content. For further analysis, the protein was submitted for AAA, n-terminal sequencing and SEC-MALS, confirming the identity of the protein as N-terminal ZZ-APRIL.

The DNA sequences for ZZ7-APRIL, ZZ9-APRIL, ZZ10-APRIL, ZZ11-APRIL, and ZZ12-APRIL are SEQ ID NOS: 43, 46, 49, 52, and 55, respectively. The protein sequences for ZZ3-APRIL, ZZ7-APRIL, ZZ9-APRIL, ZZ10-APRIL, ZZ11-APRIL, and ZZ12-APRIL are SEQ ID NOS: 41, 44, 47, 50, 53, and 56, respectively. The consensus DNA sequences for ZZ3-APRIL, ZZ7-APRIL, ZZ9-APRIL, ZZ10-APRIL, ZZ11-APRIL, and ZZ12-APRIL are SEQ ID NOS: 42, 45, 48, 51, 54, and 57, respectively.

Example 4

B-Cell Proliferation Assay Using BLyS

A vial containing $1\times10^8$ frozen, apheresed peripheral blood mononuclear cells (PBMCs) was quickly thawed in 37° C. water bath and resuspended in 25 ml B cell medium (RPMI-1640 Medium, 10% heat inactivated fetal bovine serum, 5% L-glutamine, 5% Pen/Strep) in a 50 ml tube. Cells were tested for viability using Trypan Blue (GIBCO BRL, Gaithersburg, Md.). CD19+ B cells were then isolated by positive selection using anti-CD19 coated microbeads (Miltenyi Biotech). Coated cells were then isolated on a MACS LS column (Miltenyi Biotech) The B cells were resuspended at a final concentration of $1.6\times10^6$ cells/ml in B cell medium and plated at 100 μl/well in a 96 well U bottom plate (Falcon, VWR, Seattle, Wash.).

Various soluble ZZ-APRILs as prepared in Example 3 or BLyS were added to the cells in 3 fold dilutions from 1000 ng/ml to 0 ng/ml. Final volume was 200 μl/well.

The cells were then incubated at 37° C. in a humidified incubator for 72 hours. Sixteen hours prior to harvesting, 1 μCi $^3$H thymidine was added to all wells. The cells were harvested into a 96 well filter plate (UniFilter GF/C, Packard, Meriden, Conn.) where they were harvested using a cell harvester (Packard) and collected according to manufacturer's instructions. The plates were dried at 55° C. for 20-30 minutes and the bottom of the wells were sealed with an opaque plate sealer. To each well was added 0.25 ml of scintillation fluid (Microscint-O, Packard) and the plate was read using a TopCount Microplate Scintillation Counter (Packard).

Figure 3:
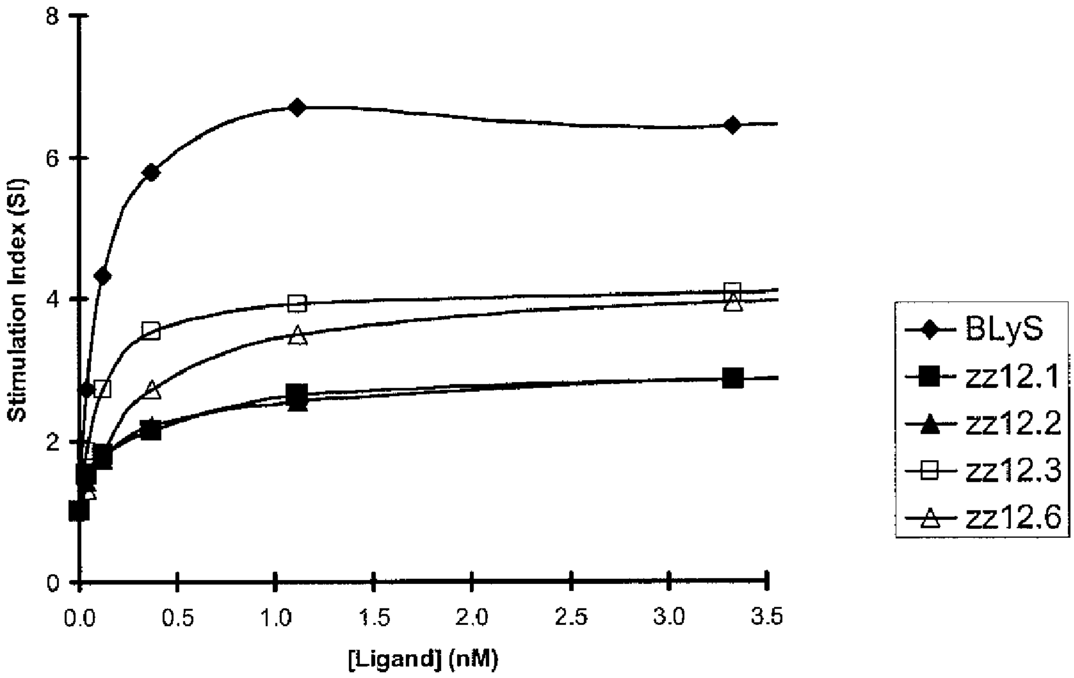
FIG. 3. graphs the results of the B-cell proliferation assay for representative ZZ12-APRIL constructs with various linkers. BLyS is a positive control.

The results of the proliferation assay are reported in FIG. 3.

Figure 5:
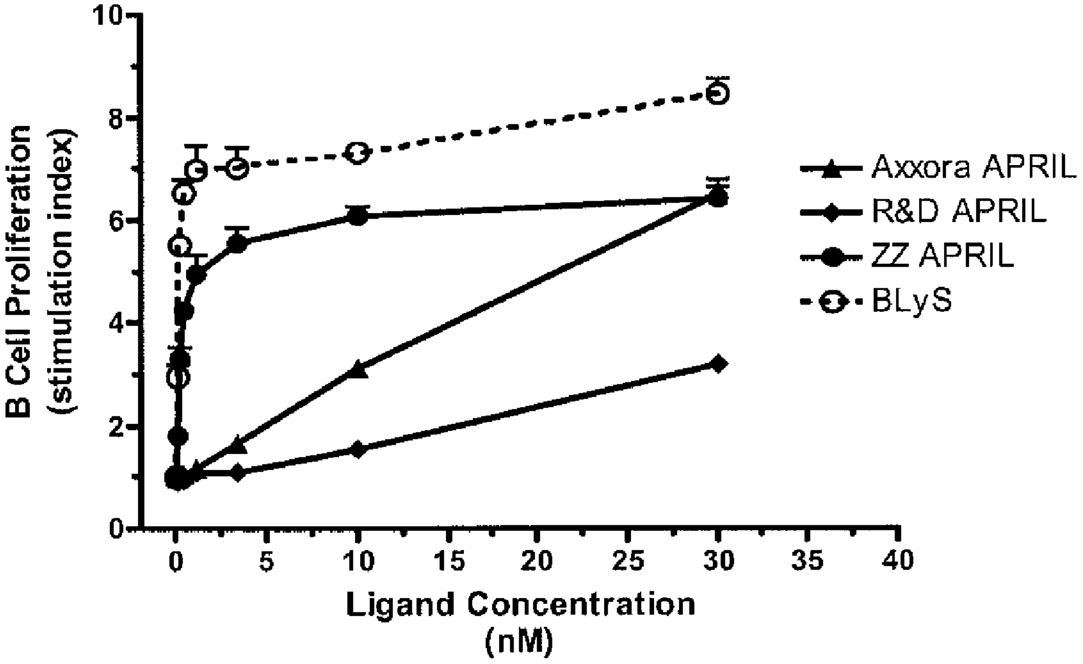
FIG. 5. graphs the results of the B-cell proliferation assay for the ZZ12-6 APRIL construct and several commercially available APRILs. BLyS is a positive control.

This assay was also used to compare the biological function of a ZZ-APRIL construct with various commercially available APRILs (Alexis APRIL and R&D APRIL). As can be seen in FIG. 5, the ZZ-APRIL better mimicked the BLyS positive control than either of the commercially available sources.

Example 5

TACI Transfected Jurkat Cell Bioassay

The TACI in vitro bioassay uses a Jurkat cell line (human acute T cell lymphocyte, KZ142, clone #24) that has been transfected with two plasmids. First, the cell line was transfected with a plasmid containing a luciferase reporter gene under control of the NF-κβ/AP-1 promoter and a neomycin-resistance gene. An appropriate clone was chosen after G418 selection. This cell line was then transfected with a plasmid containing the full length TACI cDNA under control of the CMV promoter (TACI/pZP7P) and a puromycin-resistent gene. Clones were selected with puromycin and then an appropriate cell line chosen for the assay by assessing for TACI expression by flow cytometry using TACI monoclonal antibodies.

The assay is based on recording the readout of the luciferase gene expression that is triggered by the binding of the test ligand (ZZ-APRIL) to cell surface TACI produced by from the TACI cDNA.

The transfected Jurkat cells were propagated in RPMI 1640 media without phenol red (Rosewell Park Memorial Institute, Buffalo, N.Y.) with 10% FBS added. Puromycin was added at 2 μg/ml as a selective reagent for the transfection. Sodium pyruvate and L-glutamine were also added to the media at 1% volume.

Steady-Glo Luciferase Assay System (Promega, Madison, Wis. #E2510) substrate and assay buffer were used according to manufacturer's instructions.

The assay was performed by resuspending transfected Jurkat cells in mediat to $1.6\times10^6$ cell/ml. Cells are plated on a white assay plate with 50 μl per well. Samples of ZZ-APRIL were brought to appropriate dilution and placed into a 96 well plate. Dilutions were added to the cells, at 50 μl per well. The plate was included 4 hrs in a 37° incubator. During incubation, the Steady-GLO buffer and substrate was equilibrated to room temperature. After the 4 hr. incubation, the plate was allowed to cool at room temperature for 5 minutes. Assay buffer and substrate were mixed together and added at 100 μl per well. The plates were vortexed at low setting for 1 minute to mix, then incubated at room temperature for 10 minutes. The plate was then read on a luminometer with 5 second integration.

Figure 2:
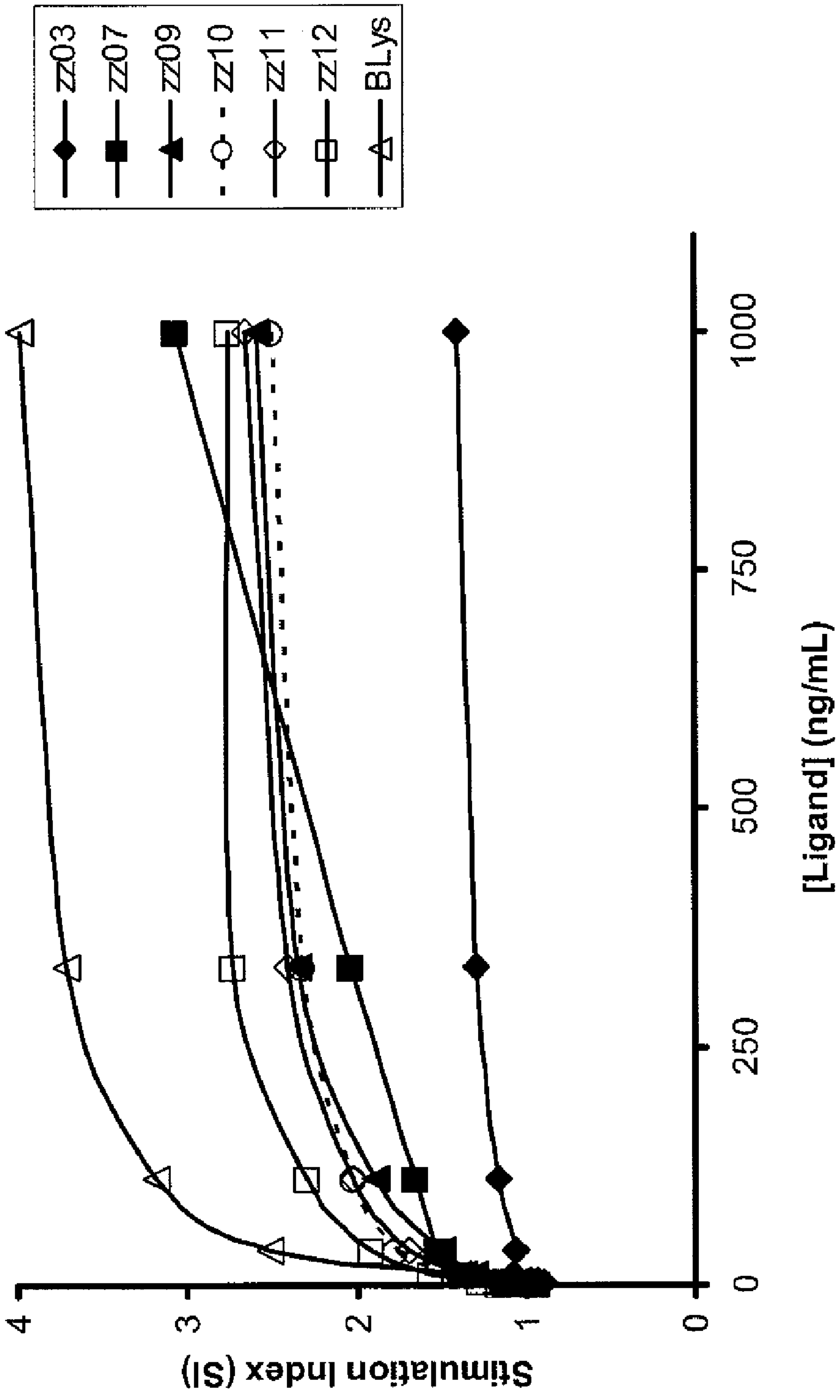
FIG. 2. graphs the results of the B-cell stimulation tests for representative ZZ-APRIL constructs at various concentrations. BLyS is a positive control.

The results of the Jurkat cell bioassay are reported in FIG. 2.

Example 6

Optimization of Linker Sequences for ZZ12

Figure 4:
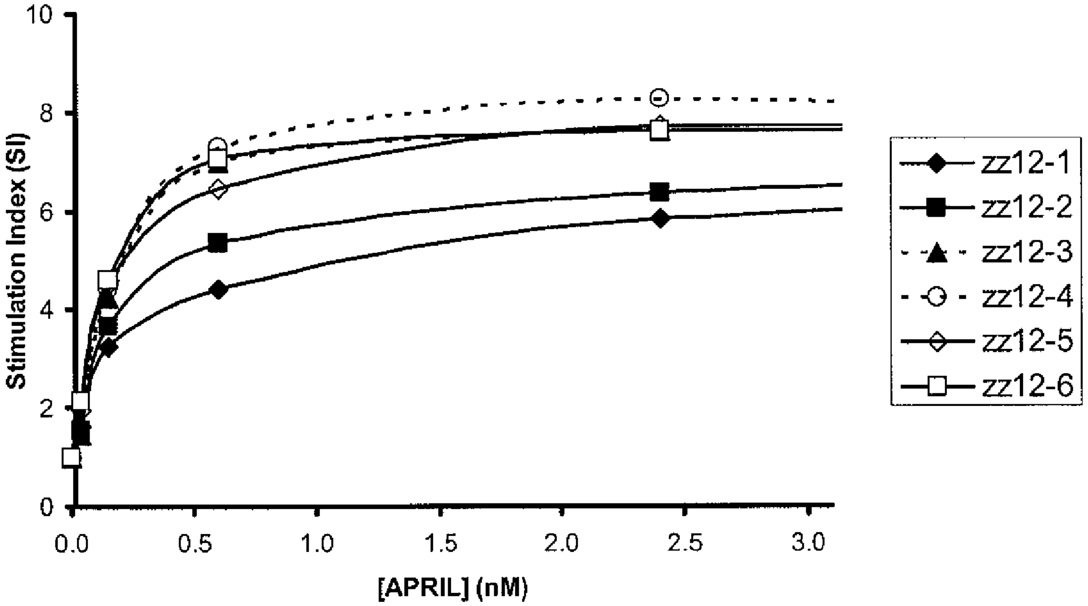
FIG. 4. graphs the results of the TACI Jurkat bioassay for representative ZZ12-APRIL constructs with various linkers. BLyS is a positive control.

Based on the results from the B-cell proliferation assay and the Jurkat cell bioassay the ZZ12 construct was selected for optimization using linker sequences. Various linker lengths in combination with the ZZ12 construct were tested for optimal biological activity using the bioassays described in Examples 4 and 5. Table 4 discloses the linker sequences tested. The results of the B-cell proliferation assay on selected linker-optimized ZZ12-APRIL constructs are reported in FIG. 3. The results of the TACI Jurkat bioassay these same constructs are reported in FIG. 4.

TABLE 4

| | abcde | fgabcd | |
|---|---|---|---|
| ZZ12.1 (SEQ ID NO: 33) | LDLLT | GDL | --APRIL[110-250] |
| ZZ12.2 (SEQ ID NO: 34) | LDLLT | GSGDL | --APRIL[110-250] |
| ZZ12.3 (SEQ ID NO: 35) | LDLLT | L | --APRIL[110-250] |
| ZZ12.4 (SEQ ID NO: 36) | LDLLT | GD | --APRIL[110-250] |
| ZZ12.5 (SEQ ID NO: 37) | LDLLT | GERSL | --APRIL[110-250] |
| ZZ12.6 (SEQ ID NO: 38) | LDLLT | RSGGGS | --APRIL[110-250] |

Example 7

Enzymatic Removal of the Zipper Domain

In order to verify that the presence of the amino-terminal zipper domain does not alter the functional and biological properties of APRIL, trypsin was used to enzymatically remove the ZZ12.6 domain from N-terminal Flag-tagged, ZymoZipper 12.6 April fusion protein (NF-ZZ12-6-APRIL). The APRIL homotrimer is unexpectedly resistant to trypsin cleavage. Additionally, two closely spaced trypsin cleavage sites are located in the junction between the zipper domain and the APRIL domain. These sites are accessible to trypsin and APRIL without the ZZ12.6 zipper can readily be obtained using the following procedure:

Approximately 24 mg of NF-ZZ12.6-APRIL at 1.2 mg/mL in 50 mM NaPO4, 250 mM NaCl 2 mM EDTA pH 7.2 was incubated for 30 minutes at 37° C. in the presence of a 1:100 mass ratio trypsin (sequencing grade, porcine, Promega). The reaction was quenched with the addition of 5 mL of 2.5 mg/mL of AEBSF trypsin inhibitor (Roche) in a similar PBS solution.

The cleaved, APRIL without the ZZ12.6 domain was separated from unreacted species using Heparin chromatography. The reaction solution was diluted to 150 mM NaCl using 17 mL cold water. The diluted solution was loaded onto a 3.4 mL AF-Heparin 650-M column (Toso Bioscience). Collected flow through analyzed by analytical heparin column chromatography and SDS-PAGE to confirm that all of the APRIL-containing molecular species were bound to the preparative heparin column. The column washed with 10 column volumes of 50 mM NaPO4, 150 mM NaCl, 1 mg/mL AEBSF pH 7.0 and then eluted using a 10 column volume gradient from 150 mM NaCl to 1M NaCl in 50 mM $NaPO_4$ pH7.0, containing 1 mg/mL AEBSF followed by a step elution with 2M NaCl. The elution of protein from the column was monitored using the absorbance of the solution at 280 nm (A280 nm). Additionally, fractions, including the load and flow through samples, were analyzed by SDS-PAGE. Two peaks were eluted, the first corresponding to intact NF-ZZ12.6-APRIL, while the second, later eluting peak corresponded to APRIL without the ZZ12.6 domain. The protein in the second peak (Heparin Eluate Pool) was processed further.

The Heparin Eluate Pool containing the APRIL without the ZZ12.6 domain was concentrated to a volume of <3 mL using a 10 kD MWCO Ultracel centrifugal membrane (Millipore) and further purified using size exclusion chromatography over a Superdex 200 16/60 column (GE Healthcare) with an isocratic elution using 50 mM $NaPO_4$ pH7.2, 250 mM NaCl. Eluate fractions were analyzed by SDS-PAGE. A small amount of aggregated material was noted in the A280 nm trace. This aggregate material was not included in the pooled eluate (Superdex 200 Eluate Pool).

The Superdex 200 Eluate Pool was further purified using 1 mL affinity resin (anti-FLAG M2 agarose resin: Sigma) with an overnight incubation at 4° C. The affinity resin binds the FLAG epitope tag (NF) amino terminal to the ZZ12.6 in the NF-ZZ12.6-APRIL molecule, and was used to remove any remaining, contaminating uncleaved NF-ZZ12.6-APRIL. The APRIL without the ZZ12.6 domain was separated from the affinity resin using a 0.22 m filtration unit (Millipore), concentrated to roughly 1 mg/mL based on analytical Heparin concentration estimate using a 5 kD MWCO Ultracel centrifugal membrane (Millipore), aliquotted and stored at −80° C.

The APRIL without the ZZ12.6 domain was characterized using analytical size exclusion chromatography with multi-angle light scattering detection and demonstrated the expected trimeric form Amino terminal sequencing verified cleavage at two of the potential trypsin sites: R83 and K90, in an approximately 2:1 ratio. The affinity of the APRIL for Atacicept (TACI-Ig) as measured using a Biacore instrument was the same for both molecular forms of APRIL (with and without the ZZ12.6). Additionally, both forms of APRIL showed comparable activity in the defined TACI-Jurkat bioassay.

While the present invention has been described with reference to the specific embodiments thereof, it is to be understood by those skilled in the art that various changes may be made and an equivalence may be substituted without departing from the true spirit and scope of the invention. In addition, many modifications may be made to adapt a particular situation, material, composition of matter, process, process step or steps, to the object, spirit and scope of the present invention. All such modifications are intended to be within the scope of the claims appended hereto.

We claim:

1. A method of preparing a trimeric protein comprising culturing a host cell transformed or transfected with an expression vector encoding a fusion protein comprising a Zymozipper (ZZ) domain which is a trimerization sequence derived from the transmembrane subunit of a virus and a heterologous protein wherein the virus is Betaretrovirus, the method further comprising removing the ZZ domain from the trimeric protein using protease digestion.

2. The method of claim 1 wherein the heterologous protein comprises the extracellular domain of said protein.

3. The method of claim 1 wherein said fusion protein is soluble.

4. The method of claim 1 wherein the Betaretrovirus is Mason Pfizer Monkey virus (MPMV).

5. The method of claim 4 wherein the ZZ domain comprises SEQ ID NO: 32.

6. The method of claim 1 wherein the fusion protein further comprises a linker sequence comprising SEQ ID NO:38.

7. A method of preparing a trimeric protein comprising culturing a host cell transformed or transfected with an expression vector encoding a fusion protein comprising a Zymozipper (ZZ) domain which is a trimerization sequence derived from the transmembrane subunit of a virus and a heterologous protein wherein the virus is Betaretrovirus, the method further comprising removing the ZZ domain from the trimeric protein using trypsin digestion.

8. The method of claim 7 wherein the heterologous protein comprises the extracellular domain of said protein.

9. The method of claim 7 wherein said fusion protein is soluble.

10. The method of claim 7 wherein the Betaretrovirus is Mason Pfizer Monkey virus (MPMV).

11. The method of claim 10 wherein the ZZ domain comprises SEQ ID NO: 32.

12. The method of claim 7 wherein the fusion protein further comprises a linker sequence comprising SEQ ID NO:38.

* * * * *

SEQUENCE LISTING

```
<160> NUMBER OF SEQ ID NOS: 58

<210> SEQ ID NO 1
<211> LENGTH: 60
<212> TYPE: DNA
<213> ORGANISM: Artificial Sequence
<220> FEATURE:
<223> OTHER INFORMATION: Primer sequence

<400> SEQUENCE: 1

agccaggaaa tccatgccga gttgagacgc ttccgtagag attataagga cgatgacgat      60


<210> SEQ ID NO 2
<211> LENGTH: 60
<212> TYPE: DNA
<213> ORGANISM: Artificial Sequence
<220> FEATURE:
<223> OTHER INFORMATION: Primer sequence

<400> SEQUENCE: 2

ggtggcgtta atgggaacca ggtgcaggac agagtgctgc ttcttctgtt tcagatctcc      60


<210> SEQ ID NO 3
<211> LENGTH: 54
<212> TYPE: DNA
<213> ORGANISM: Artificial Sequence
<220> FEATURE:
<223> OTHER INFORMATION: Primer sequence

<400> SEQUENCE: 3

gattataagg acgatgacga taagggcgga ggtggctcaa aggagtttaa caac            54


<210> SEQ ID NO 4
<211> LENGTH: 57
<212> TYPE: DNA
<213> ORGANISM: Artificial Sequence
<220> FEATURE:
<223> OTHER INFORMATION: Primer sequence

<400> SEQUENCE: 4
```

catcttcttg ttcaggttct cgatgcggcg ctccaggttg ttaaactcct ttgagcc 57

<210> SEQ ID NO 5
<211> LENGTH: 51
<212> TYPE: DNA
<213> ORGANISM: Artificial Sequence
<220> FEATURE:
<223> OTHER INFORMATION: Primer sequence

<400> SEQUENCE: 5
gagaacctga acaagaagat ggaggacggt tttctggacg tgtggaccta c 51

<210> SEQ ID NO 6
<211> LENGTH: 51
<212> TYPE: DNA
<213> ORGANISM: Artificial Sequence
<220> FEATURE:
<223> OTHER INFORMATION: Primer sequence

<400> SEQUENCE: 6
cttcttctgt ttcagatctc cctcggcgtt gtaggtccac acgtccagaa a 51

<210> SEQ ID NO 7
<211> LENGTH: 57
<212> TYPE: DNA
<213> ORGANISM: Artificial Sequence
<220> FEATURE:
<223> OTHER INFORMATION: Primer sequence

<400> SEQUENCE: 7
gattataagg acgatgacga taagggcgga ggtggctcag atgatctgcg cgaggtg 57

<210> SEQ ID NO 8
<211> LENGTH: 57
<212> TYPE: DNA
<213> ORGANISM: Artificial Sequence
<220> FEATURE:
<223> OTHER INFORMATION: Primer sequence

<400> SEQUENCE: 8
ggtcagggac ttctccagat tggagatgga cttctccacc tcgcgcagat catctga 57

<210> SEQ ID NO 9
<211> LENGTH: 57
<212> TYPE: DNA
<213> ORGANISM: Artificial Sequence
<220> FEATURE:
<223> OTHER INFORMATION: Primer sequence

<400> SEQUENCE: 9
aatctggaga agtccctgac ctccctgtcc gaggtggtgc tccagaaccg ccgcggc 57

<210> SEQ ID NO 10
<211> LENGTH: 57
<212> TYPE: DNA
<213> ORGANISM: Artificial Sequence
<220> FEATURE:
<223> OTHER INFORMATION: Primer sequence

<400> SEQUENCE: 10
cttcttctgt ttcagatctc cgaacagcag gtccaggccg cggcggttct ggagcac 57

<210> SEQ ID NO 11
<211> LENGTH: 57
<212> TYPE: DNA
<213> ORGANISM: Artificial Sequence
<220> FEATURE:

-continued

<223> OTHER INFORMATION: Primer sequence

<400> SEQUENCE: 11
gattataagg acgatgacga taagggcgga ggtggctcag atgatctggg cgccctg 57

<210> SEQ ID NO 12
<211> LENGTH: 57
<212> TYPE: DNA
<213> ORGANISM: Artificial Sequence
<220> FEATURE:
<223> OTHER INFORMATION: Primer sequence

<400> SEQUENCE: 12
ggtcagggac ttctccaggg cggacacgga tttttccagg gcgcccagat catctga 57

<210> SEQ ID NO 13
<211> LENGTH: 57
<212> TYPE: DNA
<213> ORGANISM: Artificial Sequence
<220> FEATURE:
<223> OTHER INFORMATION: Primer sequence

<400> SEQUENCE: 13
gccctggaga agtccctgac ctccctttcc gaggtcgtcc tgcagaaccg ccgcggc 57

<210> SEQ ID NO 14
<211> LENGTH: 57
<212> TYPE: DNA
<213> ORGANISM: Artificial Sequence
<220> FEATURE:
<223> OTHER INFORMATION: Primer sequence

<400> SEQUENCE: 14
cttcttctgt ttcagatctc caaaaagaag gtcaaggccg cggcggttct gcaggac 57

<210> SEQ ID NO 15
<211> LENGTH: 57
<212> TYPE: DNA
<213> ORGANISM: Artificial Sequence
<220> FEATURE:
<223> OTHER INFORMATION: Primer sequence

<400> SEQUENCE: 15
gattataagg acgatgacga taagggcgga ggtggctcag ccgacgtcca gcgcctc 57

<210> SEQ ID NO 16
<211> LENGTH: 54
<212> TYPE: DNA
<213> ORGANISM: Artificial Sequence
<220> FEATURE:
<223> OTHER INFORMATION: Primer sequence

<400> SEQUENCE: 16
ggaaagggag tcggaaagat catcgacgcc ctgctggagg cgctggacgt cggc 54

<210> SEQ ID NO 17
<211> LENGTH: 57
<212> TYPE: DNA
<213> ORGANISM: Artificial Sequence
<220> FEATURE:
<223> OTHER INFORMATION: Primer sequence

<400> SEQUENCE: 17
gatctttccg actccctttc ctccctcgcc gaggtggtgc tgcagaatcg ccgcggc 57

<210> SEQ ID NO 18

-continued

<211> LENGTH: 57
<212> TYPE: DNA
<213> ORGANISM: Artificial Sequence
<220> FEATURE:
<223> OTHER INFORMATION: Primer sequence

<400> SEQUENCE: 18
cttcttctgt ttcagatctc cgaaaagaag atcaaggccg cggcgattct gcagcac 57

<210> SEQ ID NO 19
<211> LENGTH: 57
<212> TYPE: DNA
<213> ORGANISM: Artificial Sequence
<220> FEATURE:
<223> OTHER INFORMATION: Primer sequence

<400> SEQUENCE: 19
gattataagg acgatgacga taagggcgga ggtggctcaa atggctttcg caagatg 57

<210> SEQ ID NO 20
<211> LENGTH: 57
<212> TYPE: DNA
<213> ORGANISM: Artificial Sequence
<220> FEATURE:
<223> OTHER INFORMATION: Primer sequence

<400> SEQUENCE: 20
atcgatctgt ttctggatcg taagcatggt ctgggacatc ttgcgaaagc catttga 57

<210> SEQ ID NO 21
<211> LENGTH: 57
<212> TYPE: DNA
<213> ORGANISM: Artificial Sequence
<220> FEATURE:
<223> OTHER INFORMATION: Primer sequence

<400> SEQUENCE: 21
acgatccaga aacagatcga ttcccttgcc gccgtggtgc ttcagaatcg ccgcggc 57

<210> SEQ ID NO 22
<211> LENGTH: 57
<212> TYPE: DNA
<213> ORGANISM: Artificial Sequence
<220> FEATURE:
<223> OTHER INFORMATION: Primer sequence

<400> SEQUENCE: 22
cttcttctgt ttcagatctc ccgtgaggac gtcgaggccg cggcgattct gaagcac 57

<210> SEQ ID NO 23
<211> LENGTH: 57
<212> TYPE: DNA
<213> ORGANISM: Artificial Sequence
<220> FEATURE:
<223> OTHER INFORMATION: Primer sequence

<400> SEQUENCE: 23
gattataagg acgatgacga taagggcgga ggtggctcat ccgacgtcca ggcgatc 57

<210> SEQ ID NO 24
<211> LENGTH: 57
<212> TYPE: DNA
<213> ORGANISM: Artificial Sequence
<220> FEATURE:
<223> OTHER INFORMATION: Primer sequence

<400> SEQUENCE: 24
gtcgacctgg tcctgaaggt cctggatggt ggaggagatc gcctggacgt cggatga 57

<210> SEQ ID NO 25
<211> LENGTH: 57
<212> TYPE: DNA
<213> ORGANISM: Artificial Sequence
<220> FEATURE:
<223> OTHER INFORMATION: Primer sequence

<400> SEQUENCE: 25
gaccttcagg accaggtcga ctccctggcg gaggtggtgc tgcagaatcg ccgcggc 57

<210> SEQ ID NO 26
<211> LENGTH: 57
<212> TYPE: DNA
<213> ORGANISM: Artificial Sequence
<220> FEATURE:
<223> OTHER INFORMATION: Primer sequence

<400> SEQUENCE: 26
cttcttctgt ttcagatctc ccgtaagaag gtcaaggccg cggcgattct gcagcac 57

<210> SEQ ID NO 27
<211> LENGTH: 30
<212> TYPE: PRT
<213> ORGANISM: influenza A

<400> SEQUENCE: 27

```
Lys Glu Leu Arg Glu Val Glu Lys Ser Ile Glu Asn Leu Asn Lys Lys
1               5                   10                  15

Met Glu Asp Gly Phe Leu Asp Val Leu Gln Asn Arg Arg Gly
            20                  25                  30
```

<210> SEQ ID NO 28
<211> LENGTH: 35
<212> TYPE: PRT
<213> ORGANISM: Moloney Mouse Leukemia Virus

<400> SEQUENCE: 28

```
Asp Asp Leu Arg Glu Val Glu Lys Ser Ile Ser Asn Leu Glu Lys Ser
1               5                   10                  15

Leu Thr Ser Leu Ser Glu Val Val Leu Gln Asn Arg Arg Gly Leu Asp
            20                  25                  30

Leu Leu Phe
        35
```

<210> SEQ ID NO 29
<211> LENGTH: 35
<212> TYPE: PRT
<213> ORGANISM: Mus musculus

<400> SEQUENCE: 29

```
Asp Asp Leu Gly Ala Leu Glu Lys Ser Val Ser Ala Leu Glu Lys Ser
1               5                   10                  15

Leu Thr Ser Leu Ser Glu Val Val Leu Gln Asn Arg Arg Gly Leu Asp
            20                  25                  30

Leu Leu Phe
        35
```

<210> SEQ ID NO 30
<211> LENGTH: 35
<212> TYPE: PRT
<213> ORGANISM: Mus musculus

<400> SEQUENCE: 30

```
Ala Asp Val Gln Arg Leu Gln Gln Gly Val Asp Asp Leu Ser Asp Ser
1               5                   10                  15

Leu Ser Ser Leu Ala Glu Val Val Leu Gln Asn Arg Arg Gly Leu Asp
            20                  25                  30

Leu Leu Phe
        35
```

<210> SEQ ID NO 31
<211> LENGTH: 35
<212> TYPE: PRT
<213> ORGANISM: Rat norvegicus

<400> SEQUENCE: 31

```
Asn Gly Phe Arg Lys Met Ser Gln Thr Met Leu Thr Ile Gln Lys Gln
1               5                   10                  15

Ile Asp Ser Leu Ala Ala Val Val Leu Gln Asn Arg Arg Gly Leu Asp
            20                  25                  30

Val Leu Thr
        35
```

<210> SEQ ID NO 32
<211> LENGTH: 35
<212> TYPE: PRT
<213> ORGANISM: Mason Pfizer Monkey Virus

<400> SEQUENCE: 32

```
Ser Asp Val Gln Ala Ile Ser Ser Thr Ile Gln Asp Leu Gln Asp Gln
1               5                   10                  15

Val Asp Ser Leu Ala Glu Val Val Leu Gln Asn Arg Arg Gly Leu Asp
            20                  25                  30

Leu Leu Thr
        35
```

<210> SEQ ID NO 33
<211> LENGTH: 8
<212> TYPE: PRT
<213> ORGANISM: Artificial Sequence
<220> FEATURE:
<223> OTHER INFORMATION: Final heptad plus linker

<400> SEQUENCE: 33

```
Leu Asp Leu Leu Thr Gly Asp Leu
1               5
```

<210> SEQ ID NO 34
<211> LENGTH: 10
<212> TYPE: PRT
<213> ORGANISM: Artificial Sequence
<220> FEATURE:
<223> OTHER INFORMATION: Final heptad plus linker

<400> SEQUENCE: 34

```
Leu Asp Leu Leu Thr Gly Ser Gly Asp Leu
1               5                   10
```

<210> SEQ ID NO 35
<211> LENGTH: 6
<212> TYPE: PRT
<213> ORGANISM: Artificial Sequence
<220> FEATURE:
<223> OTHER INFORMATION: Final heptad plus linker

<400> SEQUENCE: 35

```
Leu Asp Leu Leu Thr Leu
1               5


<210> SEQ ID NO 36
<211> LENGTH: 7
<212> TYPE: PRT
<213> ORGANISM: Artificial Sequence
<220> FEATURE:
<223> OTHER INFORMATION: Final heptad plus linker

<400> SEQUENCE: 36

Leu Asp Leu Leu Thr Gly Asp
1               5


<210> SEQ ID NO 37
<211> LENGTH: 10
<212> TYPE: PRT
<213> ORGANISM: Artificial Sequence
<220> FEATURE:
<223> OTHER INFORMATION: Final heptad plus linker

<400> SEQUENCE: 37

Leu Asp Leu Leu Thr Gly Glu Arg Ser Leu
1               5                   10


<210> SEQ ID NO 38
<211> LENGTH: 11
<212> TYPE: PRT
<213> ORGANISM: Artificial Sequence
<220> FEATURE:
<223> OTHER INFORMATION: Final heptad plus linker

<400> SEQUENCE: 38

Leu Asp Leu Leu Thr Arg Ser Gly Gly Gly Ser
1               5                   10


<210> SEQ ID NO 39
<211> LENGTH: 105
<212> TYPE: DNA
<213> ORGANISM: Artificial Sequence
<220> FEATURE:
<223> OTHER INFORMATION: optimized tPA leader
<220> FEATURE:
<221> NAME/KEY: CDS
<222> LOCATION: (1)...(105)

<400> SEQUENCE: 39

atg gat gca atg aag aga ggg ctc tgc tgt gtg ctg ctg ctg tgt ggc       48
Met Asp Ala Met Lys Arg Gly Leu Cys Cys Val Leu Leu Leu Cys Gly
1               5                   10                  15

gcc gtc ttc gtt tcg ctc agc cag gaa atc cat gcc gag ttg aga cgc       96
Ala Val Phe Val Ser Leu Ser Gln Glu Ile His Ala Glu Leu Arg Arg
            20                  25                  30

ttc cgt aga                                                           105
Phe Arg Arg
        35


<210> SEQ ID NO 40
<211> LENGTH: 35
<212> TYPE: PRT
<213> ORGANISM: Artificial Sequence
<220> FEATURE:
<223> OTHER INFORMATION: optimized tPA leader sequence

<400> SEQUENCE: 40

Met Asp Ala Met Lys Arg Gly Leu Cys Cys Val Leu Leu Leu Cys Gly
1               5                   10                  15
```

Ala Val Phe Val Ser Leu Ser Gln Glu Ile His Ala Glu Leu Arg Arg
20 25 30

Phe Arg Arg
35

<210> SEQ ID NO 41
<211> LENGTH: 222
<212> TYPE: PRT
<213> ORGANISM: Artificial Sequence
<220> FEATURE:
<223> OTHER INFORMATION: ZZ3-APRIL

<400> SEQUENCE: 41

Met Asp Ala Met Lys Arg Gly Leu Cys Cys Val Leu Leu Leu Cys Gly
1 5 10 15

Ala Val Phe Val Ser Leu Ser Gln Glu Ile His Ala Glu Leu Arg Arg
20 25 30

Phe Arg Arg Lys Glu Phe Asn Asn Leu Glu Arg Arg Ile Glu Asn Leu
35 40 45

Asn Lys Lys Met Glu Asp Gly Phe Leu Asp Val Trp Thr Tyr Asn Ala
50 55 60

Glu Asp Tyr Lys Asp Asp Asp Asp Lys Gly Gly Gly Gly Ser Gly Asp
65 70 75 80

Leu Lys Gln Lys Lys Gln His Ser Val Leu His Leu Val Pro Ile Asn
85 90 95

Ala Thr Ser Lys Asp Asp Ser Asp Val Thr Glu Val Met Trp Gln Pro
100 105 110

Ala Leu Arg Arg Gly Arg Gly Leu Gln Ala Gln Gly Tyr Gly Val Arg
115 120 125

Ile Gln Asp Ala Gly Val Tyr Leu Leu Tyr Ser Gln Val Leu Phe Gln
130 135 140

Asp Val Thr Phe Thr Met Gly Gln Val Val Ser Arg Glu Gly Gln Gly
145 150 155 160

Arg Gln Glu Thr Leu Phe Arg Cys Ile Arg Ser Met Pro Ser His Pro
165 170 175

Asp Arg Ala Tyr Asn Ser Cys Tyr Ser Ala Gly Val Phe His Leu His
180 185 190

Gln Gly Asp Ile Leu Ser Val Ile Ile Pro Arg Ala Arg Ala Lys Leu
195 200 205

Asn Leu Ser Pro His Gly Thr Phe Leu Gly Phe Val Lys Leu
210 215 220

<210> SEQ ID NO 42
<211> LENGTH: 666
<212> TYPE: DNA
<213> ORGANISM: Artificial Sequence
<220> FEATURE:
<223> OTHER INFORMATION: ZZ3-APRIL consensus
<220> FEATURE:
<221> NAME/KEY: misc_feature
<222> LOCATION: 9, 18, 21, 24, 33, 36, 39, 42, 48, 51, 54, 60, 63, 66, 69, 84, 90, 93, 96, 102, 105, 123, 129, 132, 144, 165, 171, 177, 183, 192, 222, 225, 228, 231, 234, 237, 243, 264, 267, 270, 276, 279, 282, 291, 294, 297, 309, 315, 318, 324, 336
<223> OTHER INFORMATION: n = A,T,C or G
<220> FEATURE:
<221> NAME/KEY: misc_feature
<222> LOCATION: 339, 342, 345, 348, 351, 354, 357, 360, 366, 372, 378, 381, 384, 396, 399, 402, 408, 411, 417, 423, 426, 438, 441, 447, 453, 459, 462, 465, 468, 474, 480, 483, 492, 495, 501, 510, 513, 519, 522, 528, 534, 537, 546, 555, 558, 561, 564
<223> OTHER INFORMATION: n = A,T,C or G
<220> FEATURE:
<221> NAME/KEY: misc_feature
<222> LOCATION: 573, 582, 591, 594, 597, 606, 609, 612, 615, 618, 624, 630, 633, 636, 642, 645, 651, 654, 660, 666
<223> OTHER INFORMATION: n = A,T,C or G

<400> SEQUENCE: 42

```
atggaygcna tgaarmgngg nytntgytgy gtnytnytny tntgyggngc ngtnttygtn     60

wsnytnwsnc argarathca ygcngarytn mgnmgnttym gnmgnaarga rttyaayaay    120

ytngarmgnm gnathgaraa yytnaayaar aaratggarg ayggnttyyt ngaygtntgg    180

acntayaayg cngargayta yaargaygay gaygayaarg gnggnggngg nwsnggngay    240

ytnaarcara araarcarca ywsngtnytn cayytngtnc cnathaaygc nacnwsnaar    300

gaygaywsng aygtnacnga rgtnatgtgg carccngcny tnmgnmgngg nmgnggnytn    360

cargcncarg gntayggngt nmgnathcar gaygcnggng tntayytnyt ntaywsncar    420

gtnytnttyc argaygtnac nttyacnatg ggncargtng tnwsnmgnga rggncarggn    480

mgncargara cnytnttymg ntgyathmgn wsnatgccnw sncayccnga ymgngcntay    540

aaywsntgyt aywsngcngg ngtnttycay ytncaycarg gngayathyt nwsngtnath    600

athccnmgng cnmgngcnaa rytnaayytn wsnccncayg gnacnttyyt nggnttygtn    660

aarytn                                                               666
```

<210> SEQ ID NO 43
<211> LENGTH: 684
<212> TYPE: DNA
<213> ORGANISM: Artificial Sequence
<220> FEATURE:
<223> OTHER INFORMATION: ZZ7-APRIL
<220> FEATURE:
<221> NAME/KEY: CDS
<222> LOCATION: (1)...(684)

<400> SEQUENCE: 43

```
atg gat gca atg aag aga ggg ctc tgc tgt gtg ctg ctg ctg tgt ggc       48
Met Asp Ala Met Lys Arg Gly Leu Cys Cys Val Leu Leu Leu Cys Gly
1               5                   10                  15

gcc gtc ttc gtt tcg ctc agc cag gaa atc cat gcc gag ttg aga cgc       96
Ala Val Phe Val Ser Leu Ser Gln Glu Ile His Ala Glu Leu Arg Arg
            20                  25                  30

ttc cgt aga gat tat aag gac gat gac gat aag ggc gga ggt ggc tca      144
Phe Arg Arg Asp Tyr Lys Asp Asp Asp Asp Lys Gly Gly Gly Gly Ser
        35                  40                  45

gat gat ctg cgc gag gtg gag aag tcc atc tcc aat ctg gag aag tcc      192
Asp Asp Leu Arg Glu Val Glu Lys Ser Ile Ser Asn Leu Glu Lys Ser
    50                  55                  60

ctg acc tcc ctg tcc gag gtg gtg ctc cag aac cgc cgc ggc ctg gac      240
Leu Thr Ser Leu Ser Glu Val Val Leu Gln Asn Arg Arg Gly Leu Asp
65                  70                  75                  80

ctg ctg ttc gga gat ctg aaa cag aag aag cag cac tct gtc ctg cac      288
Leu Leu Phe Gly Asp Leu Lys Gln Lys Lys Gln His Ser Val Leu His
                85                  90                  95

ctg gtt ccc att aac gcc acc tcc aag gat gac tcc gat gtg aca gag      336
Leu Val Pro Ile Asn Ala Thr Ser Lys Asp Asp Ser Asp Val Thr Glu
            100                 105                 110

gtg atg tgg caa cca gct ctt agg cgt ggg aga ggc cta cag gcc caa      384
Val Met Trp Gln Pro Ala Leu Arg Arg Gly Arg Gly Leu Gln Ala Gln
        115                 120                 125

gga tat ggt gtc cga atc cag gat gct gga gtt tat ctg ctg tat agc      432
Gly Tyr Gly Val Arg Ile Gln Asp Ala Gly Val Tyr Leu Leu Tyr Ser
    130                 135                 140
```

-continued

```
cag gtc ctg ttt caa gac gtg act ttc acc atg ggt cag gtg gtg tct      480
Gln Val Leu Phe Gln Asp Val Thr Phe Thr Met Gly Gln Val Val Ser
145                 150                 155                 160

cga gaa ggc caa gga agg cag gag act cta ttc cga tgt ata aga agt      528
Arg Glu Gly Gln Gly Arg Gln Glu Thr Leu Phe Arg Cys Ile Arg Ser
                165                 170                 175

atg ccc tcc cac ccg gac cgg gcc tac aac agc tgc tat agc gca ggt      576
Met Pro Ser His Pro Asp Arg Ala Tyr Asn Ser Cys Tyr Ser Ala Gly
            180                 185                 190

gtc ttc cat tta cac caa ggg gat att ctg agt gtc ata att ccc cgg      624
Val Phe His Leu His Gln Gly Asp Ile Leu Ser Val Ile Ile Pro Arg
        195                 200                 205

gca agg gcg aaa ctt aac ctc tct cca cat gga acc ttc ctg ggg ttt      672
Ala Arg Ala Lys Leu Asn Leu Ser Pro His Gly Thr Phe Leu Gly Phe
    210                 215                 220

gtg aaa ctg taa                                                      684
Val Lys Leu  *
225


<210> SEQ ID NO 44
<211> LENGTH: 227
<212> TYPE: PRT
<213> ORGANISM: Artificial Sequence
<220> FEATURE:
<223> OTHER INFORMATION: ZZ7-APRIL

<400> SEQUENCE: 44

Met Asp Ala Met Lys Arg Gly Leu Cys Cys Val Leu Leu Leu Cys Gly
1               5                   10                  15

Ala Val Phe Val Ser Leu Ser Gln Glu Ile His Ala Glu Leu Arg Arg
            20                  25                  30

Phe Arg Arg Asp Tyr Lys Asp Asp Asp Asp Lys Gly Gly Gly Gly Ser
        35                  40                  45

Asp Asp Leu Arg Glu Val Glu Lys Ser Ile Ser Asn Leu Glu Lys Ser
    50                  55                  60

Leu Thr Ser Leu Ser Glu Val Val Leu Gln Asn Arg Arg Gly Leu Asp
65                  70                  75                  80

Leu Leu Phe Gly Asp Leu Lys Gln Lys Lys Gln His Ser Val Leu His
                85                  90                  95

Leu Val Pro Ile Asn Ala Thr Ser Lys Asp Asp Ser Asp Val Thr Glu
            100                 105                 110

Val Met Trp Gln Pro Ala Leu Arg Arg Gly Arg Gly Leu Gln Ala Gln
        115                 120                 125

Gly Tyr Gly Val Arg Ile Gln Asp Ala Gly Val Tyr Leu Leu Tyr Ser
    130                 135                 140

Gln Val Leu Phe Gln Asp Val Thr Phe Thr Met Gly Gln Val Val Ser
145                 150                 155                 160

Arg Glu Gly Gln Gly Arg Gln Glu Thr Leu Phe Arg Cys Ile Arg Ser
                165                 170                 175

Met Pro Ser His Pro Asp Arg Ala Tyr Asn Ser Cys Tyr Ser Ala Gly
            180                 185                 190

Val Phe His Leu His Gln Gly Asp Ile Leu Ser Val Ile Ile Pro Arg
        195                 200                 205

Ala Arg Ala Lys Leu Asn Leu Ser Pro His Gly Thr Phe Leu Gly Phe
    210                 215                 220

Val Lys Leu
225
```

<210> SEQ ID NO 45
<211> LENGTH: 672
<212> TYPE: DNA
<213> ORGANISM: Artificial Sequence
<220> FEATURE:
<223> OTHER INFORMATION: ZZ7-APRIL consensus
<220> FEATURE:
<221> NAME/KEY: misc_feature
<222> LOCATION: 9, 18, 21, 24, 33, 36, 39, 42, 48, 51, 54, 60, 63, 66, 69, 84, 90, 93, 96, 102, 105, 132, 135, 138, 141, 144, 153, 156, 162, 171, 177, 183, 192, 195, 198, 201, 204, 207, 213, 216, 219, 228, 231, 234, 237, 243, 246, 252, 258, 279, 282
<223> OTHER INFORMATION: n = A,T,C or G
<220> FEATURE:
<221> NAME/KEY: misc_feature
<222> LOCATION: 285, 291, 294, 297, 306, 309, 312, 324, 330, 333, 342, 345, 348, 351, 354, 357, 360, 363, 366, 372, 378, 384, 387, 390, 402, 405, 408, 414, 417, 423, 429, 432, 444, 447, 453, 459, 465, 468, 471, 474, 480, 486, 489, 498, 501, 507, 516
<223> OTHER INFORMATION: n = A,T,C or G
<220> FEATURE:
<221> NAME/KEY: misc_feature
<222> LOCATION: 519, 525, 528, 534, 540, 543, 552, 561, 564, 567, 570, 579, 588, 597, 600, 603, 612, 615, 618, 621, 624, 630, 636, 639, 642, 648, 651, 657, 660, 666, 672
<223> OTHER INFORMATION: n = A,T,C or G

<400> SEQUENCE: 45

```
atggaygcna tgaarmgngg nytntgytgy gtnytnytny tntgyggngc ngtnttygtn     60

wsnytnwsnc argarathca ygcngarytn mgnmgnttym gnmgngayta yaargaygay    120

gaygayaarg gnggnggngg nwsngaygay ytnmgngarg tngaraarws nathwsnaay    180

ytngaraarw snytnacnws nytnwsngar gtngtnytnc araaymgnmg nggnytngay    240

ytnytnttyg gngayytnaa rcaraaraar carcaywsng tnytncayyt ngtnccnath    300

aaygcnacnw snaargayga ywsngaygtn acngarcarc cngcnytnmg nmgnggnmgn    360

ggnytncarg cncarggnta yggngtnmgn athcargayg cnggngtnta yytnytntay    420

wsncargtny tnttycarga ygtnacntty acnatgggnc argtngtnws nmgngarggn    480

carggnmgnc argaracnyt nttymgntgy athmgnwsna tgccnwsnca yccngaymgn    540

gcntayaayw sntgytayws ngcnggngtn ttycayytnc aycarggnga yathytnwsn    600

gtnathathc cnmgngcnmg ngcnaarytn aayytnwsnc cncayggnac nttyytnggn    660

ttygtnaary tn                                                        672
```

<210> SEQ ID NO 46
<211> LENGTH: 684
<212> TYPE: DNA
<213> ORGANISM: Artificial Sequence
<220> FEATURE:
<223> OTHER INFORMATION: ZZ9-APRIL
<220> FEATURE:
<221> NAME/KEY: CDS
<222> LOCATION: (1)...(684)

<400> SEQUENCE: 46

```
atg gat gca atg aag aga ggg ctc tgc tgt gtg ctg ctg ctg tgt ggc       48
Met Asp Ala Met Lys Arg Gly Leu Cys Cys Val Leu Leu Leu Cys Gly
1               5                   10                  15

gcc gtc ttc gtt tcg ctc agc cag gaa atc cat gcc gag ttg aga cgc       96
Ala Val Phe Val Ser Leu Ser Gln Glu Ile His Ala Glu Leu Arg Arg
            20                  25                  30

ttc cgt aga gat tat aag gac gat gac gat aag ggc gga ggt ggc tca      144
Phe Arg Arg Asp Tyr Lys Asp Asp Asp Asp Lys Gly Gly Gly Gly Ser
        35                  40                  45

gat gat ctg ggc gcc ctg gaa aaa tcc gtg tcc gcc ctg gag aag tcc      192
```

```
Asp Asp Leu Gly Ala Leu Glu Lys Ser Val Ser Ala Leu Glu Lys Ser
    50                  55                  60

ctg acc tcc ctt tcc gag gtc gtc ctg cag aac cgc cgc ggc ctt gac      240
Leu Thr Ser Leu Ser Glu Val Val Leu Gln Asn Arg Arg Gly Leu Asp
65                  70                  75                  80

ctt ctt ttt gga gat ctg aaa cag aag aag cag cac tct gtc ctg cac      288
Leu Leu Phe Gly Asp Leu Lys Gln Lys Lys Gln His Ser Val Leu His
                85                  90                  95

ctg gtt ccc att aac gcc acc tcc aag gat gac tcc gat gtg aca gag      336
Leu Val Pro Ile Asn Ala Thr Ser Lys Asp Asp Ser Asp Val Thr Glu
            100                 105                 110

gtg atg tgg caa cca gct ctt agg cgt ggg aga ggc cta cag gcc caa      384
Val Met Trp Gln Pro Ala Leu Arg Arg Gly Arg Gly Leu Gln Ala Gln
        115                 120                 125

gga tat ggt gtc cga atc cag gat gct gga gtt tat ctg ctg tat agc      432
Gly Tyr Gly Val Arg Ile Gln Asp Ala Gly Val Tyr Leu Leu Tyr Ser
    130                 135                 140

cag gtc ctg ttt caa gac gtg act ttc acc atg ggt cag gtg gtg tct      480
Gln Val Leu Phe Gln Asp Val Thr Phe Thr Met Gly Gln Val Val Ser
145                 150                 155                 160

cga gaa ggc caa gga agg cag gag act cta ttc cga tgt ata aga agt      528
Arg Glu Gly Gln Gly Arg Gln Glu Thr Leu Phe Arg Cys Ile Arg Ser
                165                 170                 175

atg ccc tcc cac ccg gac cgg gcc tac aac agc tgc tat agc gca ggt      576
Met Pro Ser His Pro Asp Arg Ala Tyr Asn Ser Cys Tyr Ser Ala Gly
            180                 185                 190

gtc ttc cat tta cac caa ggg gat att ctg agt gtc ata att ccc cgg      624
Val Phe His Leu His Gln Gly Asp Ile Leu Ser Val Ile Ile Pro Arg
        195                 200                 205

gca agg gcg aaa ctt aac ctc tct cca cat gga acc ttc ctg ggg ttt      672
Ala Arg Ala Lys Leu Asn Leu Ser Pro His Gly Thr Phe Leu Gly Phe
    210                 215                 220

gtg aaa ctg taa                                                      684
Val Lys Leu  *
225


<210> SEQ ID NO 47
<211> LENGTH: 227
<212> TYPE: PRT
<213> ORGANISM: Artificial Sequence
<220> FEATURE:
<223> OTHER INFORMATION: ZZ9-APRIL

<400> SEQUENCE: 47

Met Asp Ala Met Lys Arg Gly Leu Cys Cys Val Leu Leu Leu Cys Gly
1               5                   10                  15

Ala Val Phe Val Ser Leu Ser Gln Glu Ile His Ala Glu Leu Arg Arg
            20                  25                  30

Phe Arg Arg Asp Tyr Lys Asp Asp Asp Asp Lys Gly Gly Gly Gly Ser
        35                  40                  45

Asp Asp Leu Gly Ala Leu Glu Lys Ser Val Ser Ala Leu Glu Lys Ser
    50                  55                  60

Leu Thr Ser Leu Ser Glu Val Val Leu Gln Asn Arg Arg Gly Leu Asp
65                  70                  75                  80

Leu Leu Phe Gly Asp Leu Lys Gln Lys Lys Gln His Ser Val Leu His
                85                  90                  95

Leu Val Pro Ile Asn Ala Thr Ser Lys Asp Asp Ser Asp Val Thr Glu
            100                 105                 110

Val Met Trp Gln Pro Ala Leu Arg Arg Gly Arg Gly Leu Gln Ala Gln
        115                 120                 125
```

-continued

```
Gly Tyr Gly Val Arg Ile Gln Asp Ala Gly Val Tyr Leu Leu Tyr Ser
    130                 135                 140

Gln Val Leu Phe Gln Asp Val Thr Phe Thr Met Gly Gln Val Val Ser
145                 150                 155                 160

Arg Glu Gly Gln Gly Arg Gln Glu Thr Leu Phe Arg Cys Ile Arg Ser
                165                 170                 175

Met Pro Ser His Pro Asp Arg Ala Tyr Asn Ser Cys Tyr Ser Ala Gly
            180                 185                 190

Val Phe His Leu His Gln Gly Asp Ile Leu Ser Val Ile Ile Pro Arg
        195                 200                 205

Ala Arg Ala Lys Leu Asn Leu Ser Pro His Gly Thr Phe Leu Gly Phe
    210                 215                 220

Val Lys Leu
225


<210> SEQ ID NO 48
<211> LENGTH: 681
<212> TYPE: DNA
<213> ORGANISM: Artificial Sequence
<220> FEATURE:
<223> OTHER INFORMATION: ZZ9-APRIL consensus
<220> FEATURE:
<221> NAME/KEY: misc_feature
<222> LOCATION: 9, 18, 21, 24, 33, 36, 39, 42, 48, 51, 54, 60, 63, 66,
      69, 84, 90, 93, 96, 102, 105, 132, 135, 138, 141, 144, 153, 156,
      159, 162, 171, 174, 177, 180, 183, 192, 195, 198, 201, 204, 207,
      213, 216, 219, 228, 231, 234, 237, 243, 246, 252
<223> OTHER INFORMATION: n = A,T,C or G
<220> FEATURE:
<221> NAME/KEY: misc_feature
<222> LOCATION: 258, 279, 282, 285, 291, 294, 297, 306, 309, 312, 324,
      330, 333, 339, 351, 354, 357, 360, 363, 366, 369, 372, 375, 381,
      387, 393, 396, 399, 411, 414, 417, 423, 426, 432, 438, 441, 453,
      456, 462, 468, 474, 477, 480, 483, 489, 495, 498
<223> OTHER INFORMATION: n = A,T,C or G
<220> FEATURE:
<221> NAME/KEY: misc_feature
<222> LOCATION: 507, 510, 516, 525, 528, 534, 537, 543, 549, 552, 561,
      570, 573, 576, 579, 588, 597, 606, 609, 612, 621, 624, 627, 630,
      633, 639, 645, 648, 651, 657, 660, 666, 669, 675, 681
<223> OTHER INFORMATION: n = A,T,C or G

<400> SEQUENCE: 48

atggaygcna tgaarmgngg nytntgytgy gtnytnytny tntgyggngc ngtnttygtn      60

wsnytnwsnc argarathca ygcngarytn mgnmgnttym gnmgngayta yaargaygay     120

gaygayaarg gnggnggngg nwsngaygay ytnggngcny tngaraarws ngtnwsngcn     180

ytngaraarw snytnacnws nytnwsngar gtngtnytnc araaymgnmg nggnytngay     240

ytnytnttyg gngayytnaa rcaraaraar carcaywsng tnytncayyt ngtnccnath     300

aaygcnacnw snaargayga ywsngaygtn acngargtna tgtggcarcc ngcnytnmgn     360

mgnggnmgng gnytncargc ncarggntay ggngtnmgna thcargaygc nggngtntay     420

ytnytntayw sncargtnyt nttycargay gtnacnttya cnatgggnca rgtngtnwsn     480

mgngarggnc arggnmgnca rgaracnytn ttymgntgya thmgnwsnat gccnwsncay     540

ccngaymgng cntayaayws ntgytaywsn gcnggngtnt tycayytnca ycarggngay     600

athytnwsng tnathathcc nmgngcnmgn gcnaarytna ayytnwsncc ncayggnacn     660

ttyytnggnt tygtnaaryt n                                               681


<210> SEQ ID NO 49
<211> LENGTH: 684
<212> TYPE: DNA
```

<213> ORGANISM: Artificial Sequence
<220> FEATURE:
<223> OTHER INFORMATION: ZZ10-APRIL
<220> FEATURE:
<221> NAME/KEY: CDS
<222> LOCATION: (1)...(684)

<400> SEQUENCE: 49

```
atg gat gca atg aag aga ggg ctc tgc tgt gtg ctg ctg ctg tgt ggc       48
Met Asp Ala Met Lys Arg Gly Leu Cys Cys Val Leu Leu Leu Cys Gly
1               5                   10                  15

gcc gtc ttc gtt tcg ctc agc cag gaa atc cat gcc gag ttg aga cgc       96
Ala Val Phe Val Ser Leu Ser Gln Glu Ile His Ala Glu Leu Arg Arg
            20                  25                  30

ttc cgt aga gat tat aag gac gat gac gat aag ggc gga ggt ggc tca      144
Phe Arg Arg Asp Tyr Lys Asp Asp Asp Asp Lys Gly Gly Gly Gly Ser
        35                  40                  45

gcc gac gtc cag cgc ctc cag cag ggc gtc gat gat ctt tcc gac tcc      192
Ala Asp Val Gln Arg Leu Gln Gln Gly Val Asp Asp Leu Ser Asp Ser
    50                  55                  60

ctt tcc tcc ctc gcc gag gtg gtg ctg cag aat cgc cgc ggc ctt gat      240
Leu Ser Ser Leu Ala Glu Val Val Leu Gln Asn Arg Arg Gly Leu Asp
65                  70                  75                  80

ctt ctt ttc gga gat ctg aaa cag aag aag cag cac tct gtc ctg cac      288
Leu Leu Phe Gly Asp Leu Lys Gln Lys Lys Gln His Ser Val Leu His
                85                  90                  95

ctg gtt ccc att aac gcc acc tcc aag gat gac tcc gat gtg aca gag      336
Leu Val Pro Ile Asn Ala Thr Ser Lys Asp Asp Ser Asp Val Thr Glu
            100                 105                 110

gtg atg tgg caa cca gct ctt agg cgt ggg aga ggc cta cag gcc caa      384
Val Met Trp Gln Pro Ala Leu Arg Arg Gly Arg Gly Leu Gln Ala Gln
        115                 120                 125

gga tat ggt gtc cga atc cag gat gct gga gtt tat ctg ctg tat agc      432
Gly Tyr Gly Val Arg Ile Gln Asp Ala Gly Val Tyr Leu Leu Tyr Ser
    130                 135                 140

cag gtc ctg ttt caa gac gtg act ttc acc atg ggt cag gtg gtg tct      480
Gln Val Leu Phe Gln Asp Val Thr Phe Thr Met Gly Gln Val Val Ser
145                 150                 155                 160

cga gaa ggc caa gga agg cag gag act cta ttc cga tgt ata aga agt      528
Arg Glu Gly Gln Gly Arg Gln Glu Thr Leu Phe Arg Cys Ile Arg Ser
                165                 170                 175

atg ccc tcc cac ccg gac cgg gcc tac aac agc tgc tat agc gca ggt      576
Met Pro Ser His Pro Asp Arg Ala Tyr Asn Ser Cys Tyr Ser Ala Gly
            180                 185                 190

gtc ttc cat tta cac caa ggg gat att ctg agt gtc ata att ccc cgg      624
Val Phe His Leu His Gln Gly Asp Ile Leu Ser Val Ile Ile Pro Arg
        195                 200                 205

gca agg gcg aaa ctt aac ctc tct cca cat gga acc ttc ctg ggg ttt      672
Ala Arg Ala Lys Leu Asn Leu Ser Pro His Gly Thr Phe Leu Gly Phe
    210                 215                 220

gtg aaa ctg taa                                                      684
Val Lys Leu  *
225
```

<210> SEQ ID NO 50
<211> LENGTH: 227
<212> TYPE: PRT
<213> ORGANISM: Artificial Sequence
<220> FEATURE:
<223> OTHER INFORMATION: ZZ10-APRIL

<400> SEQUENCE: 50

```
Met Asp Ala Met Lys Arg Gly Leu Cys Cys Val Leu Leu Leu Cys Gly
```

```
1               5                   10                  15

Ala Val Phe Val Ser Leu Ser Gln Glu Ile His Ala Glu Leu Arg Arg
            20                  25                  30

Phe Arg Arg Asp Tyr Lys Asp Asp Asp Asp Lys Gly Gly Gly Gly Ser
        35                  40                  45

Ala Asp Val Gln Arg Leu Gln Gln Gly Val Asp Asp Leu Ser Asp Ser
    50                  55                  60

Leu Ser Ser Leu Ala Glu Val Val Leu Gln Asn Arg Arg Gly Leu Asp
65                  70                  75                  80

Leu Leu Phe Gly Asp Leu Lys Gln Lys Lys Gln His Ser Val Leu His
                85                  90                  95

Leu Val Pro Ile Asn Ala Thr Ser Lys Asp Asp Ser Asp Val Thr Glu
            100                 105                 110

Val Met Trp Gln Pro Ala Leu Arg Arg Gly Arg Gly Leu Gln Ala Gln
        115                 120                 125

Gly Tyr Gly Val Arg Ile Gln Asp Ala Gly Val Tyr Leu Leu Tyr Ser
    130                 135                 140

Gln Val Leu Phe Gln Asp Val Thr Phe Thr Met Gly Gln Val Val Ser
145                 150                 155                 160

Arg Glu Gly Gln Gly Arg Gln Glu Thr Leu Phe Arg Cys Ile Arg Ser
                165                 170                 175

Met Pro Ser His Pro Asp Arg Ala Tyr Asn Ser Cys Tyr Ser Ala Gly
            180                 185                 190

Val Phe His Leu His Gln Gly Asp Ile Leu Ser Val Ile Ile Pro Arg
        195                 200                 205

Ala Arg Ala Lys Leu Asn Leu Ser Pro His Gly Thr Phe Leu Gly Phe
    210                 215                 220

Val Lys Leu
225


<210> SEQ ID NO 51
<211> LENGTH: 681
<212> TYPE: DNA
<213> ORGANISM: Artificial Sequence
<220> FEATURE:
<223> OTHER INFORMATION: ZZ10-APRIL consensus
<220> FEATURE:
<221> NAME/KEY: misc_feature
<222> LOCATION: 9, 18, 21, 24, 33, 36, 39, 42, 48, 51, 54, 60, 63, 66,
      69, 84, 90, 93, 96, 102, 105, 132, 135, 138, 141, 144, 147, 153,
      159, 162, 171, 174, 183, 186, 192, 195, 198, 201, 204, 207, 213,
      216, 219, 228, 231, 234, 237, 243, 246, 252, 258
<223> OTHER INFORMATION: n = A,T,C or G
<220> FEATURE:
<221> NAME/KEY: misc_feature
<222> LOCATION: 279, 282, 285, 291, 294, 297, 306, 309, 312, 324, 330,
      333, 339, 351, 354, 357, 360, 363, 366, 369, 372, 375, 381, 387,
      393, 396, 399, 411, 414, 417, 423, 426, 432, 438, 441, 453, 456,
      462, 468, 474, 477, 480, 483, 489, 495, 498, 507
<223> OTHER INFORMATION: n = A,T,C or G
<220> FEATURE:
<221> NAME/KEY: misc_feature
<222> LOCATION: 510, 516, 525, 528, 534, 537, 543, 549, 552, 561, 570,
      573, 576, 579, 588, 597, 606, 609, 612, 621, 624, 627, 630, 633,
      639, 645, 648, 651, 657, 660, 666, 669, 675, 681
<223> OTHER INFORMATION: n = A,T,C or G

<400> SEQUENCE: 51

atggaygcna tgaarmgngg nytntgytgy gtnytnytny tntgyggngc ngtnttygtn      60

wsnytnwsnc argarathca ygcngarytn mgnmgnttym gnmgngayta yaargaygay     120

gaygayaarg gnggnggngg nwsngcngay gtncarmgny tncarcargg ngtngaygay     180
```

-continued

```
ytnwsngayw snytnwsnws nytngcngar gtngtnytnc araaymgnmg nggnytngay    240

ytnytnttyg gngayytnaa rcaraaraar carcaywsng tnytncayyt ngtnccnath    300

aaygcnacnw snaargayga ywsngaygtn acngargtna tgtggcarcc ngcnytnmgn    360

mgnggnmgng gnytncargc ncarggntay ggngtnmgna thcargaygc nggngtntay    420

ytnytntayw sncargtnyt nttycargay gtnacnttya cnatgggnca rgtngtnwsn    480

mgngarggnc arggnmgnca rgaracnytn ttymgntgya thmgnwsnat gccnwsncay    540

ccngaymgng cntayaayws ntgytaywsn gcnggngtnt tycayytnca ycarggngay    600

athytnwsng tnathathcc nmgngcnmgn gcnaarytna ayytnwsncc ncayggnacn    660

ttyytnggnt tygtnaaryt n                                              681


<210> SEQ ID NO 52
<211> LENGTH: 684
<212> TYPE: DNA
<213> ORGANISM: Artificial Sequence
<220> FEATURE:
<223> OTHER INFORMATION: ZZ11-APRIL
<220> FEATURE:
<221> NAME/KEY: CDS
<222> LOCATION: (1)...(684)

<400> SEQUENCE: 52

atg gat gca atg aag aga ggg ctc tgc tgt gtg ctg ctg ctg tgt ggc       48
Met Asp Ala Met Lys Arg Gly Leu Cys Cys Val Leu Leu Leu Cys Gly
1               5                   10                  15

gcc gtc ttc gtt tcg ctc agc cag gaa atc cat gcc gag ttg aga cgc       96
Ala Val Phe Val Ser Leu Ser Gln Glu Ile His Ala Glu Leu Arg Arg
            20                  25                  30

ttc cgt aga gat tat aag gac gat gac gat aag ggc gga ggt ggc tca      144
Phe Arg Arg Asp Tyr Lys Asp Asp Asp Asp Lys Gly Gly Gly Gly Ser
        35                  40                  45

aat ggc ttt cgc aag atg tcc cag acc atg ctt acg atc cag aaa cag      192
Asn Gly Phe Arg Lys Met Ser Gln Thr Met Leu Thr Ile Gln Lys Gln
    50                  55                  60

atc gat tcc ctt gcc gcc gtg gtg ctt cag aat cgc cgc ggc ctc gac      240
Ile Asp Ser Leu Ala Ala Val Val Leu Gln Asn Arg Arg Gly Leu Asp
65                  70                  75                  80

gtc ctc acg gga gat ctg aaa cag aag aag cag cac tct gtc ctg cac      288
Val Leu Thr Gly Asp Leu Lys Gln Lys Lys Gln His Ser Val Leu His
                85                  90                  95

ctg gtt ccc att aac gcc acc tcc aag gat gac tcc gat gtg aca gag      336
Leu Val Pro Ile Asn Ala Thr Ser Lys Asp Asp Ser Asp Val Thr Glu
            100                 105                 110

gtg atg tgg caa cca gct ctt agg cgt ggg aga ggc cta cag gcc caa      384
Val Met Trp Gln Pro Ala Leu Arg Arg Gly Arg Gly Leu Gln Ala Gln
        115                 120                 125

gga tat ggt gtc cga atc cag gat gct gga gtt tat ctg ctg tat agc      432
Gly Tyr Gly Val Arg Ile Gln Asp Ala Gly Val Tyr Leu Leu Tyr Ser
    130                 135                 140

cag gtc ctg ttt caa gac gtg act ttc acc atg ggt cag gtg gtg tct      480
Gln Val Leu Phe Gln Asp Val Thr Phe Thr Met Gly Gln Val Val Ser
145                 150                 155                 160

cga gaa ggc caa gga agg cag gag act cta ttc cga tgt ata aga agt      528
Arg Glu Gly Gln Gly Arg Gln Glu Thr Leu Phe Arg Cys Ile Arg Ser
                165                 170                 175

atg ccc tcc cac ccg gac cgg gcc tac aac agc tgc tat agc gca ggt      576
Met Pro Ser His Pro Asp Arg Ala Tyr Asn Ser Cys Tyr Ser Ala Gly
            180                 185                 190

gtc ttc cat tta cac caa ggg gat att ctg agt gtc ata att ccc cgg      624
```

```
Val Phe His Leu His Gln Gly Asp Ile Leu Ser Val Ile Ile Pro Arg
        195                 200                 205

gca agg gcg aaa ctt aac ctc tct cca cat gga acc ttc ctg ggg ttt      672
Ala Arg Ala Lys Leu Asn Leu Ser Pro His Gly Thr Phe Leu Gly Phe
    210                 215                 220

gtg aaa ctg taa                                                      684
Val Lys Leu  *
225
```

<210> SEQ ID NO 53
<211> LENGTH: 227
<212> TYPE: PRT
<213> ORGANISM: Artificial Sequence
<220> FEATURE:
<223> OTHER INFORMATION: ZZ11-APRIL

<400> SEQUENCE: 53

```
Met Asp Ala Met Lys Arg Gly Leu Cys Cys Val Leu Leu Leu Cys Gly
1               5                   10                  15

Ala Val Phe Val Ser Leu Ser Gln Glu Ile His Ala Glu Leu Arg Arg
            20                  25                  30

Phe Arg Arg Asp Tyr Lys Asp Asp Asp Asp Lys Gly Gly Gly Gly Ser
        35                  40                  45

Asn Gly Phe Arg Lys Met Ser Gln Thr Met Leu Thr Ile Gln Lys Gln
    50                  55                  60

Ile Asp Ser Leu Ala Ala Val Val Leu Gln Asn Arg Arg Gly Leu Asp
65                  70                  75                  80

Val Leu Thr Gly Asp Leu Lys Gln Lys Lys Gln His Ser Val Leu His
                85                  90                  95

Leu Val Pro Ile Asn Ala Thr Ser Lys Asp Asp Ser Asp Val Thr Glu
            100                 105                 110

Val Met Trp Gln Pro Ala Leu Arg Arg Gly Arg Gly Leu Gln Ala Gln
        115                 120                 125

Gly Tyr Gly Val Arg Ile Gln Asp Ala Gly Val Tyr Leu Leu Tyr Ser
    130                 135                 140

Gln Val Leu Phe Gln Asp Val Thr Phe Thr Met Gly Gln Val Val Ser
145                 150                 155                 160

Arg Glu Gly Gln Gly Arg Gln Glu Thr Leu Phe Arg Cys Ile Arg Ser
                165                 170                 175

Met Pro Ser His Pro Asp Arg Ala Tyr Asn Ser Cys Tyr Ser Ala Gly
            180                 185                 190

Val Phe His Leu His Gln Gly Asp Ile Leu Ser Val Ile Ile Pro Arg
        195                 200                 205

Ala Arg Ala Lys Leu Asn Leu Ser Pro His Gly Thr Phe Leu Gly Phe
    210                 215                 220

Val Lys Leu
225
```

<210> SEQ ID NO 54
<211> LENGTH: 681
<212> TYPE: DNA
<213> ORGANISM: Artificial Sequence
<220> FEATURE:
<223> OTHER INFORMATION: ZZ11-APRIL consensus
<220> FEATURE:
<221> NAME/KEY: misc_feature
<222> LOCATION: 9, 18, 21, 24, 33, 36, 39, 42, 48, 51, 54, 60, 63, 66, 69, 84, 90, 93, 96, 102, 105, 132, 135, 138, 141, 144, 150, 156, 165, 171, 177, 180, 201, 204, 207, 210, 213, 216, 219, 228, 231, 234, 237, 243, 246, 249, 252, 258, 279, 282, 285
<223> OTHER INFORMATION: n = A,T,C or G
<220> FEATURE:
<221> NAME/KEY: misc_feature
<222> LOCATION: 291, 294, 297, 306, 309, 312, 324, 330, 333, 339, 351,
354, 357, 360, 363, 366, 369, 372, 375, 381, 387, 393, 396, 399,
411, 414, 417, 423, 426, 432, 438, 441, 453, 456, 462, 468, 474,
477, 480, 483, 489, 495, 498, 507, 510, 516, 525
<223> OTHER INFORMATION: n = A,T,C or G
<220> FEATURE:
<221> NAME/KEY: misc_feature
<222> LOCATION: 528, 534, 537, 543, 549, 552, 561, 570, 573, 576, 579,
588, 597, 606, 609, 612, 621, 624, 627, 630, 633, 639, 645, 648,
651, 657, 660, 666, 669, 675, 681
<223> OTHER INFORMATION: n = A,T,C or G

<400> SEQUENCE: 54
atggaygcna tgaarmgngg nytntgytgy gtnytnytny tntgyggngc ngtnttygtn 60
wsnytnwsnc argarathca ygcngarytn mgnmgnttym gnmgngayta yaargaygay 120
gaygayaarg gnggnggngg nwsnaayggn ttymgnaara tgwsncarac natgytnacn 180
athcaraarc arathgayws nytngcngcn gtngtnytnc araaymgnmg nggnytngay 240
gtnytnacng gngayytnaa rcaraaraar carcaywsng tnytncayyt ngtnccnath 300
aaygcnacnw snaargayga ywsngaygtn acngargtna tgtggcarcc ngcnytnmgn 360
mgnggnmgng gnytncargc ncarggntay ggngtnmgna thcargaygc nggngtntay 420
ytnytntayw sncargtnyt nttycargay gtnacnttya cnatgggnca rgtngtnwsn 480
mgngarggnc arggnmgnca rgaracnytn ttymgntgya thmgnwsnat gccnwsncay 540
ccngaymgng cntayaayws ntgytaywsn gcnggngtnt tycayytnca ycarggngay 600
athytnwsng tnathathcc nmgngcnmgn gcnaarytna ayytnwsncc ncayggnacn 660
ttyytnggnt tygtnaaryt n 681

<210> SEQ ID NO 55
<211> LENGTH: 684
<212> TYPE: DNA
<213> ORGANISM: Artificial Sequence
<220> FEATURE:
<223> OTHER INFORMATION: ZZ12-APRIL
<220> FEATURE:
<221> NAME/KEY: CDS
<222> LOCATION: (1)...(684)

<400> SEQUENCE: 55

```
atg gat gca atg aag aga ggg ctc tgc tgt gtg ctg ctg ctg tgt ggc       48
Met Asp Ala Met Lys Arg Gly Leu Cys Cys Val Leu Leu Leu Cys Gly
1               5                   10                  15

gcc gtc ttc gtt tcg ctc agc cag gaa atc cat gcc gag ttg aga cgc       96
Ala Val Phe Val Ser Leu Ser Gln Glu Ile His Ala Glu Leu Arg Arg
            20                  25                  30

ttc cgt aga gat tat aag gac gat gac gat aag ggc gga ggt ggc tca      144
Phe Arg Arg Asp Tyr Lys Asp Asp Asp Asp Lys Gly Gly Gly Gly Ser
        35                  40                  45

tcc gac gtc cag gcg atc tcc tcc acc atc cag gac ctt cag gac cag      192
Ser Asp Val Gln Ala Ile Ser Ser Thr Ile Gln Asp Leu Gln Asp Gln
    50                  55                  60

gtc gac tcc ctg gcg gag gtg gtg ctg cag aat cgc cgc ggc ctt gac      240
Val Asp Ser Leu Ala Glu Val Val Leu Gln Asn Arg Arg Gly Leu Asp
65                  70                  75                  80

ctt ctt acg gga gat ctg aaa cag aag aag cag cac tct gtc ctg cac      288
Leu Leu Thr Gly Asp Leu Lys Gln Lys Lys Gln His Ser Val Leu His
                85                  90                  95

ctg gtt ccc att aac gcc acc tcc aag gat gac tcc gat gtg aca gag      336
Leu Val Pro Ile Asn Ala Thr Ser Lys Asp Asp Ser Asp Val Thr Glu
            100                 105                 110
```

```
gtg atg tgg caa cca gct ctt agg cgt ggg aga ggc cta cag gcc caa      384
Val Met Trp Gln Pro Ala Leu Arg Arg Gly Arg Gly Leu Gln Ala Gln
        115                 120                 125

gga tat ggt gtc cga atc cag gat gct gga gtt tat ctg ctg tat agc      432
Gly Tyr Gly Val Arg Ile Gln Asp Ala Gly Val Tyr Leu Leu Tyr Ser
    130                 135                 140

cag gtc ctg ttt caa gac gtg act ttc acc atg ggt cag gtg gtg tct      480
Gln Val Leu Phe Gln Asp Val Thr Phe Thr Met Gly Gln Val Val Ser
145                 150                 155                 160

cga gaa ggc caa gga agg cag gag act cta ttc cga tgt ata aga agt      528
Arg Glu Gly Gln Gly Arg Gln Glu Thr Leu Phe Arg Cys Ile Arg Ser
                165                 170                 175

atg ccc tcc cac ccg gac cgg gcc tac aac agc tgc tat agc gca ggt      576
Met Pro Ser His Pro Asp Arg Ala Tyr Asn Ser Cys Tyr Ser Ala Gly
            180                 185                 190

gtc ttc cat tta cac caa ggg gat att ctg agt gtc ata att ccc cgg      624
Val Phe His Leu His Gln Gly Asp Ile Leu Ser Val Ile Ile Pro Arg
        195                 200                 205

gca agg gcg aaa ctt aac ctc tct cca cat gga acc ttc ctg ggg ttt      672
Ala Arg Ala Lys Leu Asn Leu Ser Pro His Gly Thr Phe Leu Gly Phe
    210                 215                 220

gtg aaa ctg taa                                                      684
Val Lys Leu  *
225


<210> SEQ ID NO 56
<211> LENGTH: 227
<212> TYPE: PRT
<213> ORGANISM: Artificial Sequence
<220> FEATURE:
<223> OTHER INFORMATION: ZZ12-APRIL

<400> SEQUENCE: 56

Met Asp Ala Met Lys Arg Gly Leu Cys Cys Val Leu Leu Leu Cys Gly
1               5                   10                  15

Ala Val Phe Val Ser Leu Ser Gln Glu Ile His Ala Glu Leu Arg Arg
            20                  25                  30

Phe Arg Arg Asp Tyr Lys Asp Asp Asp Asp Lys Gly Gly Gly Gly Ser
        35                  40                  45

Ser Asp Val Gln Ala Ile Ser Ser Thr Ile Gln Asp Leu Gln Asp Gln
    50                  55                  60

Val Asp Ser Leu Ala Glu Val Val Leu Gln Asn Arg Arg Gly Leu Asp
65                  70                  75                  80

Leu Leu Thr Gly Asp Leu Lys Gln Lys Lys Gln His Ser Val Leu His
                85                  90                  95

Leu Val Pro Ile Asn Ala Thr Ser Lys Asp Asp Ser Asp Val Thr Glu
            100                 105                 110

Val Met Trp Gln Pro Ala Leu Arg Arg Gly Arg Gly Leu Gln Ala Gln
        115                 120                 125

Gly Tyr Gly Val Arg Ile Gln Asp Ala Gly Val Tyr Leu Leu Tyr Ser
    130                 135                 140

Gln Val Leu Phe Gln Asp Val Thr Phe Thr Met Gly Gln Val Val Ser
145                 150                 155                 160

Arg Glu Gly Gln Gly Arg Gln Glu Thr Leu Phe Arg Cys Ile Arg Ser
                165                 170                 175

Met Pro Ser His Pro Asp Arg Ala Tyr Asn Ser Cys Tyr Ser Ala Gly
            180                 185                 190

Val Phe His Leu His Gln Gly Asp Ile Leu Ser Val Ile Ile Pro Arg
```

```
        195                 200                 205

Ala Arg Ala Lys Leu Asn Leu Ser Pro His Gly Thr Phe Leu Gly Phe
    210                 215                 220

Val Lys Leu
225
```

<210> SEQ ID NO 57
<211> LENGTH: 681
<212> TYPE: DNA
<213> ORGANISM: Artificial Sequence
<220> FEATURE:
<223> OTHER INFORMATION: ZZ12-APRIL consensus
<220> FEATURE:
<221> NAME/KEY: misc_feature
<222> LOCATION: 9, 18, 21, 24, 33, 36, 39, 42, 48, 51, 54, 60, 63, 66, 69, 84, 90, 93, 96, 102, 105, 132, 135, 138, 141, 144, 147, 153, 159, 165, 168, 171, 183, 195, 201, 204, 207, 213, 216, 219, 228, 231, 234, 237, 243, 246, 249, 252, 258, 279, 282
<223> OTHER INFORMATION: n = A,T,C or G
<220> FEATURE:
<221> NAME/KEY: misc_feature
<222> LOCATION: 285, 291, 294, 297, 306, 309, 312, 324, 330, 333, 339, 351, 354, 357, 360, 363, 366, 369, 372, 375, 381, 387, 393, 396, 399, 411, 414, 417, 423, 426, 432, 438, 441, 453, 456, 462, 468, 474, 477, 480, 483, 489, 495, 498, 507, 510, 516
<223> OTHER INFORMATION: n = A,T,C or G
<220> FEATURE:
<221> NAME/KEY: misc_feature
<222> LOCATION: 525, 528, 534, 537, 543, 549, 552, 561, 570, 573, 576, 579, 588, 597, 606, 609, 612, 621, 624, 627, 630, 633, 639, 645, 648, 651, 657, 660, 666, 669, 675, 681
<223> OTHER INFORMATION: n = A,T,C or G

<400> SEQUENCE: 57

```
atggaygcna tgaarmgngg nytntgytgy gtnytnytny tntgyggngc ngtnttygtn     60

wsnytnwsnc argarathca ygcngarytn mgnmgnttym gnmgngayta yaargaygay    120

gaygayaarg gnggnggngg nwsnwsngay gtncargcna thwsnwsnac nathcargay    180

ytncargayc argtngayws nytngcngar gtngtnytnc araaymgnmg nggnytngay    240

ytnytnacng gngayytnaa rcaraaraar carcaywsng tnytncayyt ngtnccnath    300

aaygcnacnw snaargayga ywsngaygtn acngargtna tgtggcarcc ngcnytnmgn    360

mgnggnmgng gnytncargc ncarggntay ggngtnmgna thcargaygc nggngtntay    420

ytnytntayw sncargtnyt nttycargay gtnacnttya cnatgggnca rgtngtnwsn    480

mgngarggnc arggnmgnca rgaracnytn ttymgntgya thmgnwsnat gccnwsncay    540

ccngaymgng cntayaayws ntgytaywsn gcnggngtnt tycayytnca ycarggngay    600

athytnwsng tnathathcc nmgngcnmgn gcnaarytna ayytnwsncc ncayggnacn    660

ttyytnggnt tygtnaaryt n                                               681
```

<210> SEQ ID NO 58
<211> LENGTH: 8
<212> TYPE: PRT
<213> ORGANISM: Artificial Sequence
<220> FEATURE:
<223> OTHER INFORMATION: FLAG tag

<400> SEQUENCE: 58

```
Asp Tyr Lys Asp Asp Asp Asp Lys
1               5
```